United States Patent [19]

Novak et al.

[11] Patent Number: 5,498,775

[45] Date of Patent: Mar. 12, 1996

[54] POLYANIONIC BENZYLGLYCOSIDES AS INHIBITORS OF SMOOTH MUSCLE CELL PROLIFERATION

[75] Inventors: Sarah T. A. Novak, Cary, N.C.; Richard M. Soll, Lawrenceville; John W. Ellingboe, Princeton, both of N.J.; Thomas T. Nguyen, Philadelphia, Pa.

[73] Assignee: American Home Products Corporation, Madison, N.J.

[21] Appl. No.: 335,278

[22] Filed: Nov. 7, 1994

[51] Int. Cl.$^6$ .......................... A61K 31/70; C07H 15/00
[52] U.S. Cl. .......................... 514/25; 514/460; 536/17.5; 536/17.9; 549/476; 549/478
[58] Field of Search .................. 549/476, 478; 514/460, 25; 536/17.5, 17.9

[56] References Cited

U.S. PATENT DOCUMENTS

| | | | |
|---|---|---|---|
| 4,431,636 | 2/1984 | Schaub et al. | 424/180 |
| 4,431,637 | 2/1984 | Upeslacis et al. | 424/180 |
| 4,431,638 | 2/1984 | Schaub et al. | 424/180 |
| 4,435,387 | 3/1984 | Schaub et al. | 424/180 |
| 5,019,562 | 5/1991 | Folkman et al. | 514/58 |

FOREIGN PATENT DOCUMENTS

| | | |
|---|---|---|
| 0312086 | 4/1989 | European Pat. Off. . |
| 0312087 | 4/1989 | European Pat. Off. . |
| 9309790 | 5/1993 | WIPO . |

OTHER PUBLICATIONS

Clowes, et al., J. Vasc. Surg. 13, 885–891 (1991).
Raines et al., Br. Heart J. 69 (Suppl.), S30 (1993).
Isik et al., Am. J. Pathol., 141 (5) 1139–1149 (1992).
Herrmann et al., Drugs 46(1), 18–52 (1993).
Herrman et al., Drugs 46(1) 249–262 (1993).
Weissberg et al., Cardiovascular Res. 27 1191–1198 (1993).
Castellot et al., Seminars in Thrombosis and Hemostasis, 13(4), 489–503 (1987).
Borman, Chemical and Engineering News, p. 27, Jun. 28, 1993.
Reilly et al., Drug Development Research, 29, 137–147 (1993).

(List continued on next page.)

*Primary Examiner*—Richard D. Lovering
*Assistant Examiner*—Catherine Kilby Scalzo
*Attorney, Agent, or Firm*—Steven R. Eck

[57] ABSTRACT

This invention relates to the use of polyanionic benzylglycosides as smooth muscle cell proliferation inhibitors and as therapeutic compositions for treating diseases and conditions which are characterized by excessive smooth muscle proliferation, such as restenosis. The compounds of this invention are those of formula I

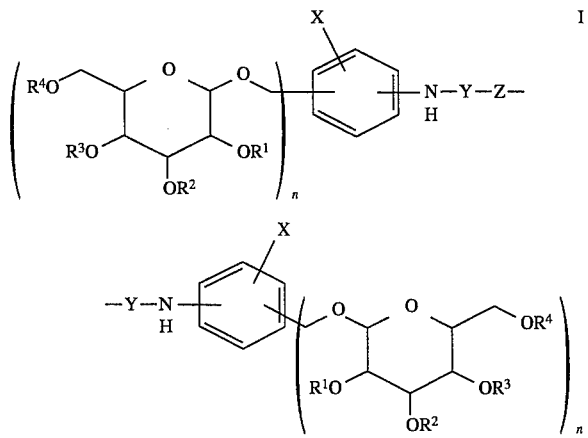

wherein each of $R^1$, $R^2$, $R^3$, and $R^4$ are, independently, H, $SO_3M$, or

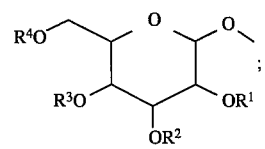

and each oligosaccharide group contains 1 to 3 sugar groups;

M is lithium, sodium, potassium, or ammonium;

n is 1 or 2;

X is a halogen, lower alkyl having 1 to 6 carbon atoms, or lower alkoxy having 1 to 6 carbon atoms;

Y is carbonyl or sulfonyl;

Z is alkyl from 1 to 12 carbon atoms,

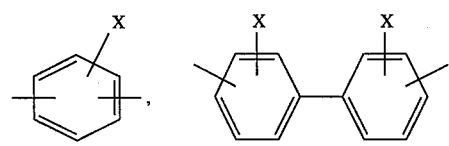

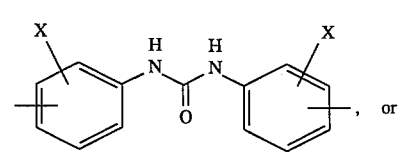

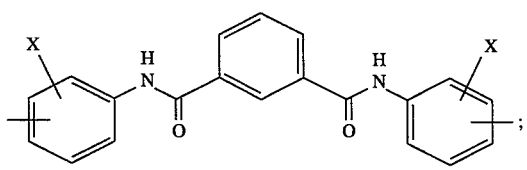

and X is as defined above;
or a pharmaceutically acceptable salt thereof.

23 Claims, No Drawings

OTHER PUBLICATIONS

Casscells, Circulation, 86, 723–729 (1992).
Reidy et al., Endothelial Cell Dysfunction, 31–48, Ed. Plenum Press, NY (1992).
Wight, Arteriosclerosis 1989, 9, 1–20 (1989).
Schmid et al., Seminar in Thrombosis and Hemostasis, 19, Suppl. 1, 155–159 (1993).
Amann et al., Seminars in Thrombosis and Hemostasis, 19, Suppl. 1, 160–163 (1993).
Radhakrishnamurthy et al., Atherosclerosis, 60, 141–149 (1986).
Maffrand et al., Seminars in Thrombosis and Hemostasis, 17, Suppl. 2, 186–198 (1991).
Weisz et al., Angiogensis: Key Principle–Science–Technology–Medicine p. 107 (1992).
Hermann et al., Arteriosclerosis and Thrombosis, 13, 924–931 (1993).

POLYANIONIC BENZYLGLYCOSIDES AS INHIBITORS OF SMOOTH MUSCLE CELL PROLIFERATION

This invention relates to polyanionic benzylglycosides and their use as smooth muscle cell proliferation inhibitors and as therapeutic compositions for treating diseases and conditions which are characterized by excessive smooth muscle proliferation, such as restenosis.

BACKGROUND OF THE INVENTION

All forms of vascular reconstruction such as angioplasty and vein bypass procedures effect a response to injury that ultimately leads to smooth muscle cell (SMC) proliferation and, subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermarts, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191). Indeed, an important therapeutic consideration is to promote reendotheliaztion of the injured area concurrent with SMC proliferation inhibition (Casscells, W. *Circulation* 1992, 86, 722; Reidy, M. A.; Lidner, V. in *Endothelial Cell Dysfunctions*, Simionescu, N. and Simionescu M., Ed. Plenum Press, N.Y. N.Y., (1992), 31).

The glycosaminoglycans heparin and heparin sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489; Wight, T. N. *Arteriosclerosis* 1989, 9, 1). However, the full clinical benefits of heparin, heparin fragments, chemically modified heparin, low molecular weight heparins, and other heparin mimicking anionic polysaccharides may be compromised due to other pharmacological liabilites (excessive bleeding arising from anticoagulation effects, in particular) coupled with heterogeneity of the various preparations (Borman, S. *Chemical and Engineering News*, 1993, June 28, 27; Schmid, K. M.; Preisack, M.; Voelker, W.; Sujatta M.; Karsch, K. R. *Seminars in Thrombosis and Hemostasis* 1993, 19 (Suppl. 1), 155; Amann, F. W.; Neuenschwander, C.; Meyer, B. *Seminars in Thrombosis and Hemostasis* 1993, 19 (Suppl. 1 ), 160; Radhakrishnamurthy, B.; Sharma, C.; Bhandaru, R. R.; Berenson, G. S.; Stanzani, L.; Mastacchi, R. *Atherosclerosis*, 1986 60, 141; Maffrand, J. P.; Hervert, M. M.; Bernat, A.; Defreyn, G.; Delevassee, D.; Savi, P.; Pinot, J. J.; Sampol, J. *Seminars in Thrombosis and Hernostasis*, 1991, 17 (Suppl. 2), 186). Since the anticoagulant effects of many of these agents are independent of SMC antiproliferative activity, it would be expected that polyanionic agents which are more homogenous in composition and of more defined molecular structure would exhibit a more desirable profile with fewer side effects associated with the aforementioned anionic polysaccharides.

Prior Art

WO 92/18546 discloses specific sequences of heparin, obtainable in pure form through synthesis or heparin fragment isolation, which exhibit SMC antiproliferation activity. Beta-Cyclodextrin tetradecasulfate has been described as a smooth muscle cell proliferation inhibitor and as an effective inhibitor of restenosis (Weisz, P. B.; Hermann, H. C.; Joullie, M. M.; Kumor, K.; Levine, E. M.; Macarak, E. J.; Weiner, D. B. *Angiogenesis: Key Principle—Science—Technology—Medicine*—Steiner R., Weisz, P. B.; Langer, R. Eds. Birkhauser Verlag, Basel Switzerland, 1992, pg. 107; Hermann, H. C.; Okada, S. S.; Hozakowska, E.; LeVeen, R. F.; Golden, M. A.; Tomaszewski J. E.; Weisz, P. B.; Barnathan E. S. *Arteriosclerosis and Thrombosis* 1993, 13, 924; Reilly, C. F.; Fujita, T.; McFall, R. C.; Stabilito, I. I.; Wai-si E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residue. EP 312087 A2 and EP 312086 A2 discloses antithrombotic and anticoagulant properties of sulfated bisaldonic acid amides.

U.S. Pat. Nos. 4,431,636, 4,431,637, 4,431,638, and 4,435,387 describe polysulfated, thio- and oxy-aryl glycoside derivatives as modulators of the complement system.

The compounds of the present invention differ from all of the prior art in that the compounds (a) are benzylglycosides which bear no structural resemblance to heparin, sulfated cyclodextrins, or to sulfated factobionic acid dimers, (b) contain no more than three contiguous sugar residues (trisaccharides) and (b) are of defined structure.

DESCRIPTION OF THE INVENTION

This invention describes the composition and utility of sulfated benzylglycosides of formula I

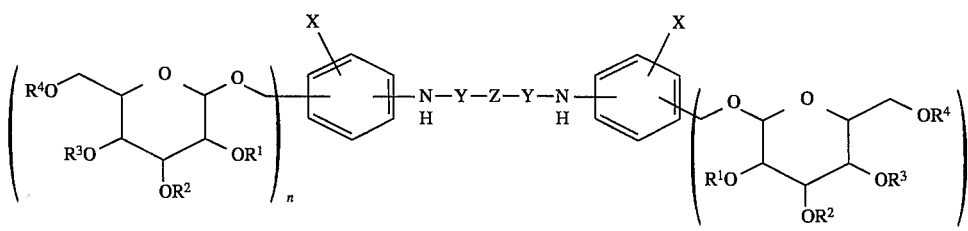

wherein each of $R^1$, $R^2$, $R^3$, and $R^4$ are, independently, H, $SO_3M$, or

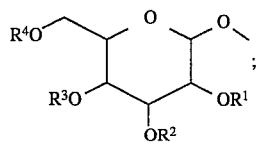

and each oligosaccharide group contains 1 to 3 sugar groups;
M is lithium, sodium, potassium, or ammonium;
n is 1 or 2;
X is a hydrogen, halogen, lower alkyl having 1 to 6 carbon atoms, or lower alkoxy having 1 to 6 carbon atoms;
Y is carbonyl or sulfonyl;
Z is alkyl having from 1 to 12 carbon atoms,

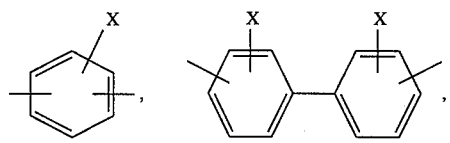

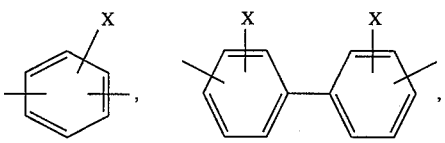

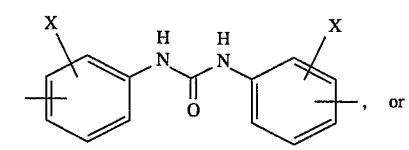

and X is as defined above;
or a pharmaceutically acceptable salt thereof.

A more preferred aspect or embodiment of this invention is the compounds of formula I:

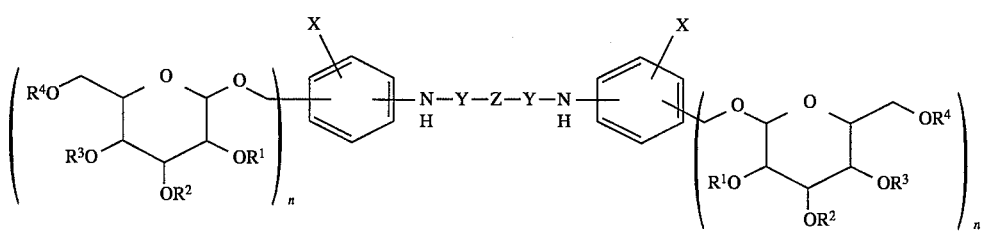

wherein
each of $R^1$, $R^2$, $R^3$, and $R^4$ are, independently, H, $SO_3M$, or

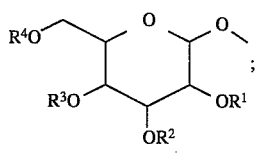

and each oligosaccharide group contains 1 or 2 sugar groups;
M is lithium, sodium, potassium, or ammonium;
n is 1 or 2; X is a hydrogen, halogen, lower alkyl having 1 to 6 carbon atoms, or lower alkoxy having 1 to 6 carbon atoms;
Y is carbonyl or sulfonyl;
Z is alkyl having from 1 to 12 carbon atoms,

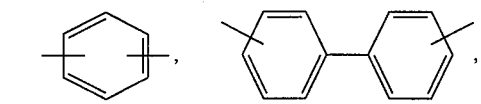

or a pharmaceutically acceptable salt thereof.
The most preferred compounds of this invention are:
Dodecanedioic acid bis{[2-methyl-5-(hepta-O-sulfato-β-D-cellobiosyloxymethyl)phenyl] amide}tetradecasodium salt or a pharmaceutically acceptable salt thereof;
N,N'-Bis[5-(hepta-O-sulfato-β-D-cellobiosyloxymethyl)-2-methylphenyl]terephthalamide tetradecasodium salt or a pharmaceutically acceptable salt thereof;
Biphenyl-4,4'-dicarboxylic acid bis{[5-(hepta-O-sulfato-β-D-cellobiosyloxymethyl)-2-methylphenyl] amide}tetradecasodium salt or a pharmaceutically acceptable salt thereof;
N,N'-Bis[5-(hepta-O-sulfato-β-D-cellobiosyloxymethyl)-2-methylphenyl]isophthalamide tetradecasodium salt or a pharmaceutically acceptable salt thereof;
Decanedioic acid bis{[3,5-bis(hepta-O-sulfato-β-D-cellobiosyloxymethyl)phenyl] amide}octacosasodium salt or a pharmaceutically acceptable salt thereof;
Biphenyl-4,4'-dicarboxylic acid bis{[3,5-bis(hepta-O-sulfato-β-D-cellobiosyloxymethyl)phenyl] amide}octacosasodium salt or a pharmaceutically acceptable salt thereof;
Biphenyl-4,4'-dicarboxylic acid bis{[3,5-bis-(hepta-O-sulfato-β-D-lactosyloxymethyl)phenyl] amide}octacosasodium salt or a pharmaceutically acceptable salt thereof;
Biphenyl-4,4'-dicarboxylic acid bis{[3,5-(bis-(hepta-O-sulfato-β-D-maltosyoxymethyl)phenyl] amide}octacosasodium salt or a pharmaceutically acceptable salt thereof;
Biphenyl-4,4'-dicarboxylic acid bis{[3,5-bis-(tetra-O-sulfato-β-D-glucosyloxymethyl)phenyl] amide}hexadecasodium salt or a pharmaceutically acceptable salt thereof;

Biphenyl-4,4'-dicarboxylic acid bis{[2-chloro-5-(hepta-O-sulfato-β-D-cellobiosyloxymethyl)phenyl]amide}tetradecasodium salt or a pharmaceutically acceptable salt thereof;

Biphenyl-4,4'-dicarboxylic acid bis{[4-chloro-2-(hepta-O-sulfato-β-D-cellobiosyloxymethyl)phenyl]amide}tetradecasodium salt or a pharmaceutically acceptable salt thereof;

N,N'-Bis{3-[2-methyl-5-(hepta-O-sulfato-β-D-maltosyloxymethyl)phenylcarbamoyl] phenyl}isophthalamide tetradecasodium salt or a pharmaceutically acceptable salt thereof.

PROCESS OF THE INVENTION

The compounds of the present invention are prepared according to the general sequence of reactions outlined in the Scheme below:

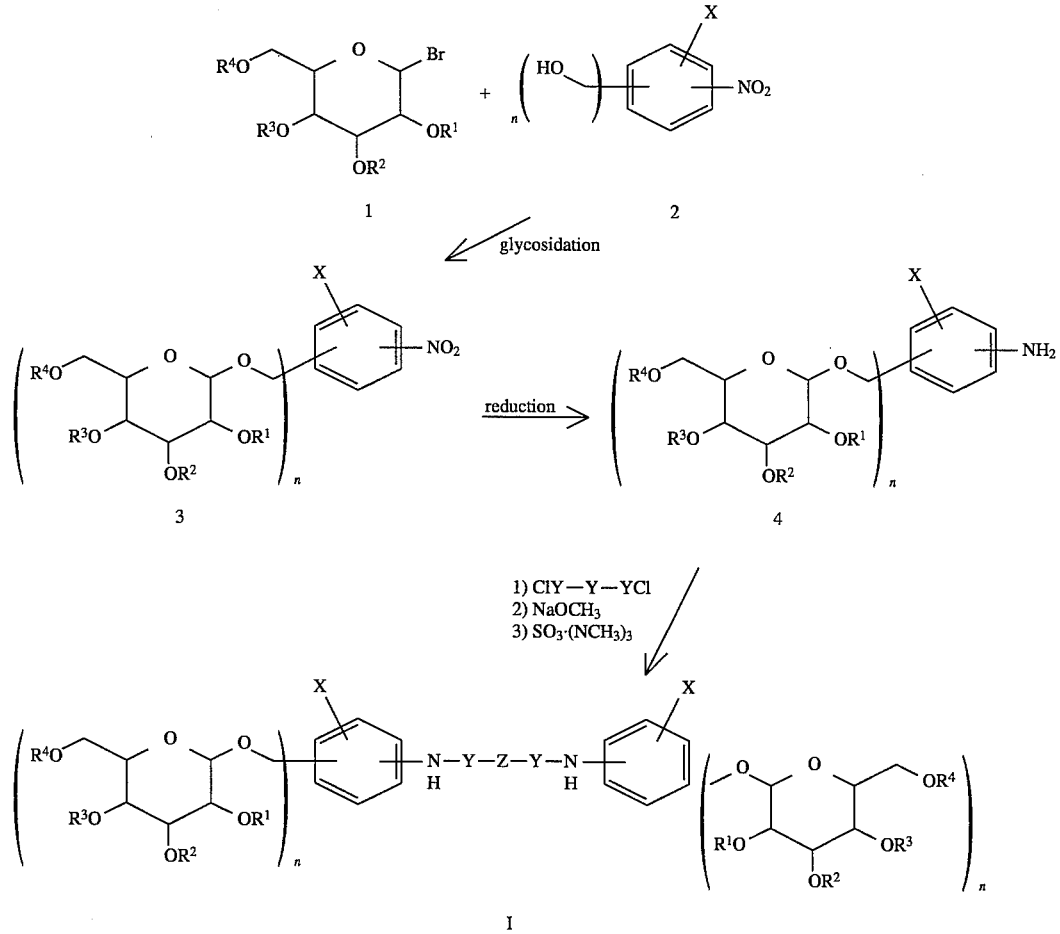

N,N'-Bis[3,5-bis-(hepta-O-sulfato-β-D-cellobiosyloxymethyl)phenyl]succinamide octacosasodium salt or a pharmaceutically acceptable salt thereof;

N,N'-Bis[3,5-bis(hepta-O-sulfato-β-D-cellobiosyloxymethyl)phenyl]terephthalamide octacosasodium salt or a pharmaceutically acceptable salt thereof;

Biphenyl-4,4'-disulfonic acid bis{[2-methyl-5-(hepta-O-sulfato-β-D-cellobiosyloxymethyl)phenyl]amide}tetradecasodium salt or a pharmaceutically acceptable salt thereof;

N,N'-Bis[2-methyl-5-(2,3,4,6-tetra-O-sulfato-β-D-glucopyranosyloxymethyl)phenyl] succinamide octasodium salt or a pharmaceutically acceptable salt thereof;

3,3'-[N,N'-Ureido]-bis{N-[2-methyl-5-(hepta-O-sulfato-β-D-maltosyloxymethyl)phenyl] }benzamide tetradecasodium salt or a pharmaceutically acceptable salt thereof;

3,3'-(N,N'-Ureido)bis-({N-[2-chloro-5-(hepta-O-sulfato-β-D-cellobiosyloxymethyl)phenyl] }benzamide) tetradecasodium salt or a pharmaceutically acceptable salt thereof;

wherein R, n, X, Y, and Z are as defined above.

Thus, a glycosyl bromide 1 is coupled with a benzylic alcohol 2 in the presence of a catalyst such as a mercuric bromide, mercuric cyanide, silver triflate, or silver perchlorate in an aprotic solvent such as dichloromethane, ether, toluene, or nitromethane at temperatures ranging from −40° C. to ambient temperature to yield glycoside 3. Reduction of the nitro group of 3 can be accomplished with a reducing agent such as stannous chloride in a polar aprotic solvent such as ethyl acetate at ambient temperature to reflux, or by catalytic hydrogenation in the presence of a catalyst such as palladium on carbon gives an anilino compound 4. Coupling of 4 with a his acid chloride or sulfonyl chloride ClY-Z-YCl can be done in the presence of an amine base such as triethylamine or diisopropylethylamine in an aprotic solvent such as dichloromethane or tetrahydrofuran, hydrolysis of any acetate groups present on the sugars with a base such as sodium methoxide in methanol or aqueous sodium hydroxide in methanol at ambient temperature to reflux, and sulfation of some or all of the free hydroxyl groups on the sugars can be completed with a reagent such as sulfur trioxide-trimethylamine complex or sulfur trioxide-pyridine complex in a polar aprotic solvent such as dimethylformamide or dimethylsulfoxide at temperatures ranging from 0° C. to 100° C. yields the target compounds I.

Alternatively, the sulfate groups can be introduced into compound 3 (after hydrolysis of any acetate groups). Sulfated compound 3 is then reduced to give sulfated 4 and coupled with ClY-Z-YCl to yield I.

This invention is also directed to pharmaceutical compositions comprised of sulfated benzylglycosides either alone or in combination with excipients (i.e. pharmaceutically acceptable materials with no pharmacological effect). Such compositions are useful for diseases which are characterized by excessive smooth muscle cell proliferation, such as restinosis, most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of this invention are thus useful for treating these diseases and states.

The compounds of this invention may be administered systemically, for example by intravenous injection, typically ranging from 0.1 to 10 mg/kg/h over 5- 30 days, or by subcutaneous injection at lower dose, by oral administration at higher dose than intravenous injection. Localized delivery of the compounds of this invention may also be achieved by transmembrane, transdermal, or other topical administrative routes using appropriate continuous release devices such as supporting matrix, where applicable. The compositions of the invention may be formulated with conventional excipients, such as a filler, a disintegrating agent, a binder, a lubricant, a flavoring agent and the like. These are formulated in a conventional manner. It is understood that the compounds of this invention may be administered in any manner and at any concentration that is efficacious to the particular recipient. The manner of delivery and composition and concentration of the dose will be determined on an individual basis by the physician or other skilled medical professional treating the recipient.

Effects on Cell Proliferation

A. Cell Sources

The ability of the compounds of the present invention to inhibit smooth muscle cell proliferation and modulate endothelial cell growth was established using isolated aortic cells obtained from commercial sources or, for certain species, prepared in-house. Cell lines used in this study include human and porcine aortic smooth muscle cells and human aortic endothelial cells. Human aortic cell lines were obtained from Clonetics Corporation (San Diego).

Porcine aortas were received from a local slaughterhouse. The material was iced during transit. The aorta was scrupulously cleansed of fatty tissue and rinsed in sterile phosphate-buffered saline with 2% antibiotic/antimycotic (Gibco catalog # 600-5240 AG). The tissue was then digested in 10–15 mL of "Enzyme Mixture" containing collagenase type I, 165 U/mL; elasta. se type III, 15 U/mL; BSA, 2 mg/mL; and soybean trypsin inhibitor, 0.375 mg/mL followed by incubation at 37° C. under 5% $CO_2$ for 10–15 min. After this treatment, the outer surface adventitia was easily removed by peeling with forceps. The aorta was then longitudinally cut and laid open and the endothelial layer was removed by scraping.

The medial layer of cells was rinsed in enzyme solution, and placed in a new 100 mm dish with 10 mL of enzyme solution. The aorta was minced using a fine pair of scissors and digested for 2–3 h at 37° C. in 30 mL of fresh enzyme solution. After digestion, the tissue was homogenized using a sterile Pasteur pipette with a fire polished tip or an eppendorf pipetier with a 200–1000 mL sterile pipette tip. The suspension was then centrifuged for 10 min at 8000 rpm and the pellet was suspended in 4–6 mL of fresh medium and plated onto 4–6 100 mm flasks with vented caps. Cells were allowed to grow to confluence and split using 0.25% trypsin. Cells were evaluated for purity and overall quality using antibody to SMC actin.

B. Effects of compounds on cell proliferation using $^3H$ Thymidine incorporation Cells were assayed in early passage (generally passage 3–7) at sub-confluent conditions. Cultures were grown in 16 mm (24 well) multi-well culture dishes in media 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer preincubations, in general, experiments were initiated with the addition of compound, $^3H$ thymidine and serum/growth factor to serum deprived synchronized cells and results are reported in this invention accordingly. Growth factor and serum stimulations were optimized for each cell type.

Compounds were added to each well at 50 fold dilution (20 µL/well) and the plates were incubated for 24–36 h at 37° C. in 5% $CO_2$. In this series, all compounds were found to be $H_2O$ soluble and hence, test compounds were initially diluted in $H_2O$ and serially diluted into media. Compounds were routinely assayed at 1, 10, and 100 µM. As a control, grade II porcine intestinal mucosal heparin (sodium salt) from Sigma (H-7005) was routinely assayed in all cell preparations at concentrations from 0.1 to 100 µg/mL.

At the completion of the experiment, plates were placed on ice, washed three times with ice cold PBS and incubated in ice cold 10% trichloroacetic acid (TCA) for 30 min to remove acid soluble proteins. Solution was transferred to scintillation vials containing 0.4N HCl (500 µL/vial to neutralize NaOH) and each well was rinsed two times with water (500 µL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data was expressed as a percent of control from which $IC_{50}$s could be determined. The compounds of the present invention are effective inhibitors of smooth muscle cell proliferation as summarized in Table I. Furthermore, the compounds of the present invention exhibit human smooth muscle cell (HAOSMC) antiproliferative activity in the case where proliferation is driven by either 10% fetal bovine serum (FBS) or platelet derived growth factor (PDGF; human recombinant PDGF-AB purchased from Upstate Biotechnology Inc., Lake Placid, N.Y.). For example, the sulfated compound of Example 18 inhibits HAOSMC proliferation driven by FBS ($IC_{50}$ 200 nM) as well as by 5 ng/mL of PDGF ($IC_{50}$ 380 nM).

C. Effect on Endothelial Cell Growth vs. Smooth Muscle Cell Proliferation

The promotion of endothelial cell proliferation concurrent with inhibition of smooth muscle cell proliferation is an important consideration for inhibiting the exaggerated response to injury arising from vascular reconstruction. The compounds of the present invention enhance human endothelial cell growth driven by 2% FBS at doses inhibitory towards human smooth muscle cell proliferation driven by 10% FBS as represented by the sulfated compound of Example 18 as shown in FIG. 1.

D. Cytotoxicity

Visually, all cells were found to tolerate high levels of all compounds quite well, however to insure that no toxicity was present, cytotoxicity of compounds was examined using a commercial modification of the MTT (3-[4,5-dimethylthiazol-2-yl]- 2,5-diphenyltetrazolium bromide) assay. Briefly, cells were again grown in 24 well plates to 70–80% confluency and, as before, serum deprived for 24–48 h prior to initiation of the experimental protocol. To insure that the MTT assay monitored toxicity rather than proliferation, cells were incubated with 250 μM drug in fresh medium without serum for 24 h at 37° C. in a humidified $CO_2$ incubator. Upon completion of the compound treatment, MTT (3-[4, 5-dimethylthiazol-2-yl]-2,5-diphenyltetrazolium bromide) indicator dye was added for 4 h at 37° C. Cells were then lysed and aliquots from each well were transferred to a 96 well plate for analysis. Absorbance at 570 nm wavelength with a reference wavelength of 630 nm was recorded using an ELISA plate reader. Results are reported as percent viable using no drug (100% viable) and pre-solubilization (0% viable) standards. No toxicity was observed up to 250 μM with sulfated compounds of Examples 10–25 and Example 26 (Step 5).

Anticoagulant Activity

The anticlotting activity of the compounds of this invention was evaluated in a partial thromboplastin time (APTT) assay using normal human plasma collected from 5 donors using the procedure of Fenichel el. al. (*Clin. Chem.* 1964, 10, 69). A BBL Fibrometer automatic precesion coagulation timer utilizing a 0.3 mL probe was employed. An Ellagic acid activated partial thromboplastin was used for these experiments. This reagent was added to human citrated plasma equilibrated at 37° C. in a plastic well in the clot timer. Calcium at 37° C. was added, the clot timer was started and the time for fibrin clot formation (in seconds) was recorded. The effect of the compounds, added to plasma, over a concentration of 12.5–200 μg/mL was determined. Any plasma which did not clot after 240 seconds was assigned a clotting time of 240 seconds. An unfractionated heparin comparator was used over the concentration range of 1.25–10 μg/mL. Clotting tests at all concentrations were run in triplicate. Analysis of variance for a randomized block design was used to determine the significance of differences observed in the clotting times. The potency is reported relative to heparin, wherein ratio >1 indicates weaker activity relative to heparin on a μg/mL comparison.

TABLE I

| SULFATED COMPOUND OF EXAMPLE | Porcine Smooth Muscle Cell Anti-proliferation $IC_{50}$ or (% Inhibition at × concentration) | Anticoagulation Activity (APTT) Relative to Heparin |
| --- | --- | --- |
| EXAMPLE 26, STEP 5 | 118 μM | nt |
| EXAMPLE 25 | (8% inhibition at 50 μg/mL) | nt |
| EXAMPLE 10 | 161 μM | nt |
| EXAMPLE 24 | 58 μM | nt |
| EXAMPLE 11 | 117 μM | nt |
| EXAMPLE 12 | 72 μM | nt |
| EXAMPLE 13 | 40.5–80 μM | nt |
| EXAMPLE 14 | 3 μM | 6.7 |
| EXAMPLE 15 | 4.7 μM | 2.0–2.3 |
| EXAMPLE 20 | 45 μM | nt |
| EXAMPLE 21 | 43 μM | nt |
| EXAMPLE 22 | 5.2–22 μM | 2.0 |
| EXAMPLE 16 | 3.6 μM | 2.2 |
| EXAMPLE 17 | 23–50.8 μM | insignificant activity at 50 μg/mL |
| EXAMPLE 18 | 0.85 μM | 2.1 |
| EXAMPLE 19 | (10–50% inhibition at 20 μM) | nt |
| EXAMPLE 23 heparin (H-7005) | 9.5–40 μM (45–83% inhibition at 50 μg/mL) | 2.0 1 | nt = not tested

Specific procedures are described in the following examples. These examples are given to illustrate the invention and should not be construed as limiting the invention set forth in the appended claims.

EXAMPLE 1

Step 1

5-(Hepta-O-acetyl-β-D-maltosyloymethyl)-2-methyl-1-nitrobenzene

To 4.0 g (24 mmol) of 4-methyl-3-nitrobenzyl alcohol and 20.0 g (29 mmol) of acetobromo-α-maltose in 60 mL of $CH_3NO_2$ was added 6.15 g (24 mmol) of $Hg(CN)_2$ and 6.91 g (19 mmol) of $HgBr_2$. After stirring at ambient temperature overnight, the reaction was quenched with sat. NaCl and was stirred for 20 min. The reaction mixture was extracted into $CH_2Cl_2$. The organic phase was washed with sat. NaCl, dried ($MgSO_4$) and flash chromatographed (1:2 and 1:1 EtOAc/petroleum ether). Rechromatography using ether/petroleum ether (3:1, then 4:1, then 100:0) gave 7.97 g of the title compound as a colorless solid: $^1$H-NMR ($CDCl_3$, 300 MHz) δ7.92 (s, 1 H), 7.41 (d, 1 H), 7.32 (d, 1 H), 5.42 (d, 1 H), 5.36 (t, 1 H), 5.25 (t, 1 H), 5.06 (t, 1 H), 4.8–5.0 (m, 3 H), 4.65 (d, 1 H), 4.62 (d, 1 H), 4.54 (dd, 1 H), 4.2– 4.3 (m, 2 H), 3.9–4.1 (m, 3 H), 3.65–3.71 (m, 1 H), 2.60 (s, 3 H), 2.16 (s, 3 H), 2.11 (s, 3 H), 2.04 (s, 3 H), 2.03 (s, 6 H), 2.01 (s, 3 H), and 2.00 ppm (s, 3 H).

Step 2

5-(Hepta-O-acetyl-β-D-maltosyloxymethyl)-2-methylhenylamine

Procedure A:

A mixture of 4.0 g (5.09 mmol) of 5-(hepta-O-acetyl-β-D-maltosyloxymethyl)- 2-methyl-1-nitrobenzene prepared in Example 1 and 8.00 g (35 mmol) of $SnCl_2·H_2O$ in 100 mL EtOAc was heated at reflux for 2 h. The reaction mixture was cooled to room temperature and quenched with sat. $NaHCO_3$. After stirring for 15 min, the mixture was diluted with $CH_2Cl_2$ (200 mL) and filtered through solka floc (CH₂Cl₂). The organic phase was dried (MgSO₄) and concentrated. Flash chromatography (EtOAc/CH₂Cl₂, 1:5, then 1:4, then 1:2, then 1:1) gave 3.42 g (89% yield) of the title compound as a colorless foam: ¹H-NMR (CDCl₃, 300 MHz) δ7.01 (d, 1 H), 6.63 (s, 1 H), 6.62 (d, 1 It), 5.41 (d, 1 H), 5.39 (t, 1 H), 5.20 (t, 1 H), 5.05 (t, 1 H), 4.82–4.90 (m, 2 H), 4.75 (d, 1 H), 4.54 (d, 1 H), 4.51 (d, 1 H, 4.26 (dd, 2 H), 3.95–4.01 (m, 3 H), 3.63–3.67 (m, 1 H), 2.17 (s, 6 H), 2.11 (s, 3 H), 2.03 (s, 6 H), 2.00 (s, 3 H), and 1.99 ppm (s, 6 H).

Procedure B

A solution of 31.1 g (39.6 mmol) of 5-(hepta-O-acetyl-β-D-maltosyloxymethyl)- 2-methyl-1-nitrobenzene prepared in step 1 of Example 1 was hydrogenated at 50 psi over 10% Pd/C (10.0 g) for 1 h. The catalyst was removed by filtration and the filtrate was concentrated to give a white foam. Trituration with water gave 28.0 g (94%) of the title compound as a white solid, mp 154°–156 ° C.

EXAMPLE 2

5-(Hepta-O-acetyl-β-D-cellobiosyloxymethyl)-2-methyl-1-nitrobenzene

The title compound was prepared in 47% yield by the procedure of step 1 of Example 1 using 4-methyl-3-nitrobenzyl alcohol and acetobromocellobiose. Purification was achieved by flash chromatography (EtOAc/petroleum ether, 1:2 to 1:1 to 2:1): ¹H-NMR (CDCl₃, 300 MHz) δ7.91 (s, 1 H), 7.40 (d, 1 H), 7.32 (d, 1 H), 4.80–5.20 (m, 6 H), 4.40–4.80 (m, 4 H), 4.36 (dd, 1 H), 4.02–4.13 (m, 2 H), 3.81 (t, 1 H), 3.60–3.68 (m, 2 H), 2.60 (s, 3 It), 2.14 (s, 3 H), 2.08 (s, 3 H), 2.03 (s, 3 H), 2.02 (s, 3 H), 2.01 (s, 3 H), and 1.98 ppm (s, 3 H).

Step 2

5-(Hepta-O-acetyl-β-D-cellobiosyloxymethyl)-2-methylphenylamine

The title compound, mp 180°–182° C., was prepared in 62% yield from 5-(hepta-O-acetyl-β-D-cellobiosyloxymethyl)-2-methyl-1-nitrobenzene using Procedure A of step 2 of Example 1. Purification was achieved by flash chromatography (EtOAc/petroleum ether, 1:1 to 2:1): ¹H-NMR (DMSO-d₆, 400 MHz) δ6.86 (d, 1 H), 6.48 (d, 1 H), 6.36 (dd, 1 H), 5.24 (t, 1 H), 5.10 (m, 1 H), 4.80–4.90 (m, 3 H), 4.61–4.72 (m, 2 H), 4.56 (d, 1 H), 4.30–4.31 (m, 2 H), 4.22 (dd, 1 H), 4.08 (dd, 1 H), 3.99–4.03 (m, 1 H), 3.94 (dd, 1 H), 3.73–3.81 (m, 2 H), 2.10 (s, 3 H), 2.10 (s, 3 H), 2.00 (s, 3 H), 1.98 (s, 3 H), 1.96 (s, 3 H), 1.95 (s, 3 H), 1.94 (s, 3 H), and 1.91 ppm (s, 1 H); mass spectrum (+FAB) m/z 778. Anal. Calcd. for $C_{34}H_{46}NO_{18}$: C, 53.97; H, 6.13; N, 1.85. Found: C, 53.67; H, 5.92; N, 1.62.

EXAMPLE 3

Step 1

5-(Hepta-O-acetyl-β-D-cellobiosyloxymethyl)-2-chloro-1-nitrobenzene

The title compound was prepared in 45% yield by the procedure described in step 1 of Example 1 using 4-chloro-3-nitrobenzyl alcohol and acetobromocellobiose: ¹H-NMR (CDCl₃, 300 MHz) δ7.82 (d, 1 H), 7.53 (d, 1 H), 7.42 (dd, 1 H), 4.80–5.20 (m, 5 H), 4.73 (d, 1 H), 4.51–4.66 (m, 4 H), 4.30–4.40 (m, 1 H), 4.03–4.11 (m, 2 H), 3.81 (t, 1 H), 3.60–3.68 (m, 2 H), 2.13 (s, 3 H), 2.09 (s, 3 H), 2.06 (s, 3 H), 2.03 (s, 3 H), 2.01 (s, 3 H), 2.01 (s, 3 H), 1.99 (s, 3 H), and 1.57 ppm (s, 3 H).

Step 2

5-(Hepta-O-acetyl-β-D-cellobiosyloxymethyl)-2-chlorophenylamine

The title compound was prepared from 5-(hepta-O-acetyl-β-D-cellobiosyloxymethyl)- 2-chloro-1-nitrobenzene in 61% yield as a solid by trituration with ether using Procedure A of step 1 of Example 1: ¹H-NMR (CDCl₃, 300 MHz) δ7.20 (d, 1 H), 6.75 (s, 1 H), 6.60 (d, 1 H), 4.89–5.19 (m, 5 H), 4.73 (d, 1 H), 4.47–4.60 (m, 4 H), 4.36 (dd, 1 H), 4.02–4.13 (m, 2 H), 3.80 (t, 1 H), 3.55–3.67 (m, 2 H), 2.14 (s, 3 H), 2.08 (s, 3 H), 2.03 (s, 3 H), 2.02 (s, 6 It), 2.01 (s, 3 H), and 2.00 ppm (s, 3 H).

EXAMPLE 4

Step 1

2-(Hepta-O-acetyl-β-D-cellobiosyloxymethyl)-4-chloro-1-nitrobenzene

The title compound was prepared in 47% yield by the procedure of step 1 of Example 1 using 5-chloro-2-nitrobenzyl alcohol and acetobromocellobiose. Partial purification was achieved using flash chromatography (CH₂Cl₂/EtOAc, 6:1) and the product used as is in the next reaction: ¹H-NMR (CDCl₃, 300 MHz) δ8.09 (d, 1 H), 7.71 (d, 1 H), 7.43 (dd, 1 H), 4.90–5.25 (m, 8 H), 4.63 (d, 1 H), 4.52 (d, 1 H), 4.49 (d, 1 H), 4.38 (dd, 1 H), 4.03–4.16 (m, 3 H), 3.79 (t, 1 H), 3.60–3.68 (m, 2 H), 2.13 (s, 3 H), 2.10 (s, 6 H), 2.04 (s, 6 H), 2.01 (s, 3 H), and 1.98 ppm (s, 3 H).

Step 2

2-(Hepta-O-acetyl-β-D-cellobiosyloxymethyl)-4-chlorophenylamine

The title compound was prepared in 55% yield from 2-(hepta-O-acetyl-β-D-cellobiosyloxymethyl)- 5-chloro-1-nitrobenzene by Procedure A of step 2 of Example 1. Purification was achieved by trituration with ether: ¹H-NMR (CDCl₃, 300 MHz) δ7.11 (dd, 1 H), 7.04 (d, 1 H), 6.65 (d, 1 H), 5.03–5.18 (m, 3 H), 4.88–4.97 (m, 2 H), 4.45–4.80 (m, 5 H), 4.36 (dd, 1 H), 4.02–4.13 (m, 2 H), 3.60–3.81 (m, 3 H), 2.16 (s, 3 H), 2.08 (s, 3 H), 2.04 (s, 3 H), 2.01 (s, 6 H), 2.00 (s, 3 H), and 1.98 ppm (s, 3 H).

EXAMPLE 5

Step 1

5-(Tetra-O-acetyl-β-D-glucopyranosyloymethyl)-2-methyl-1-nitrobenzene

The title compound was prepared in 54% yield by the procedure described in step 1 of Example 1 using α-D-glucopyranosyl bromide tetraacetate and 4-methyl-3-nitrobenzyl alcohol: ¹H-NMR (CDCl₃, 300 MHz) δ7.92 (d, 1 H), 7.43 (dd, 1 H), 7.33 (d, 1 H), 5.06–5.24 (m, 3 H), 4.92 (d, 1 H), 4.66 (d, 1 H), 4.59 (d, 1 H), 4.28 (dd, 1 H), 4.18 (dd, 1 H), 3.68–3.72 (m, 1 H), 2.60 (s, 3 H), 2.11 (s, 3 H), 2.07 (s, 3 H), 2.03 (s, 3 H), and 2.01 ppm (s, 3 H).

Step 2

5-(Tetra-O-acetyl-D-glucopyranosyloxymethyl)-2-methylphenylamine

The title compound was prepared in 63% yield by Procedure A of step 2 of Example 1 from 5-(tetra-O-acetyl-β-D-glucopyranosyloxymethyl)-2-methylnitrobenzene and purified by trituration of the crude reaction mixture with ether: ¹H-NMR (CDCl₃, 300 MHz) δ7.02 (d, 1 H), 6.64 (s, I H), 6.63 (d, 1 H), 5.02–5.17 (m, 3 H), 4.79 (d, 1 H), 4.50–4.55 (m, 2 H), 4.29 (dd, 1 H), 4.17 (dd, 1 H), 3.64–3.68 (m, 1 H), 2.18 (s, 3 H), 2.11 (s, 3 H), 2.02 (s, 3 H), 2.01 (s, 3 H), and 2.00 ppm (s, 3 H).

EXAMPLE 6

Step 1

3,5-Bis(hepta-O-acetyl-β-D-cellobiosyloxymelhyl)-1-nitrobenzene

The title compound was prepared in 42% yield by the procedure described in step 1 of Example 1 using one equivalent of 5-nitro-m-xylene-α,α'-diol, two equivalents of acetobromocellobiose, and two equivalents of all other reagents. Purification was achieved by flash chromatography (EtOAc/CH$_2$Cl$_2$, 3:1) and trituration with ether: $^1$H-NMR (CDCl$_3$, 300 MHz) δ8.10 (s, 2 H), 7.48 (s, 1 H), 4.88–5.30 (m, 12 H), 4.68 (d, 2 H), 4.52–4.59 (m, 6 H), 4.38 (dd, 2 H), 4.00–4.13 (m, 4 H), 3.82 (t, 2 H), 3.58–3.68 (m, 4 H), 2.13 (s, 6 H), 2.08 (s, 6 H), 2.07 (s, 6 H), 2.03 (s, 12 H), 2.01 (s, 6 H), and 1.98 ppm (s, 6 H).

Step 2

3,5-Bis(hepta-O-acetyl-β-D-cellobiosyloxymethyl) phenylamine

The title compound was prepared in 54% yield by Procedure A of step 2 of Example 1 using 3,5-bis(hepta-O-acetyl-β-D-cellobiosyloxymethyl)-1-nitrobenzene. Purification was achieved by flash chromatography (EtOAc/petroleum ether, 1:1): $^1$H-NMR (CDCl$_3$, 300 MHz) δ6.73 (bs, 2 H), 6.67 (bs, 1 H), 5.03–5.30 (m, 6 H), 4.97 (d, 2 H), 4.91 (d, 2 H), 4.75 (d, 2 H), 4.49–4.61 (m, 6 H), 4.37 (dd, 2 H), 4.02–4.13 (m, 6 H), 3.81 (t, 2 H), 3.57–3.69 (m, 4 H), 2.15 (s, 6 H), 2.08 (s, 6 H), 2.03 (s, 6 H), 2.01 (s, 18 H), and 1.98 ppm (s, 6 H).

EXAMPLE 7

Step 1

3,5-Bis(hepta-O-acetyl-β-D-lactosyloxymethyl)-1-nitrobenzene

The title compound was prepared by the procedure described in step 1 of Example 1 using 1 equivalent of 5-nitro-m-xylene-α,α'-diol, two equivalents of acetobromolactose, and two equivalents of all other reagents. Purification was achieved initially by flash chromatography (EtOAc/CH$_2$Cl$_2$ (3:1)) and then rechromatography first with toluene/EtOAc (1:1) and then with EtOAc/CH$_2$Cl$_2$ (1:4 to 1:2) to give partially pure product which was used directly in the next reaction.

Step 2

3,5-Bis(hepta-O-acetyl-β-D-lactosyloxymethyl) phenylamine

The title compound was prepared by procedure A of step 2 of Example 1 using 3,5-bis(hepta-O-acetyl-β-D-lactosyloxymethyl)-1-nitrobenzene. Partial purification was achieved by flash chromatography (CH$_2$Cl$_2$/EtOAc (2:1 to 1:2)) and then rechromatography (CH$_2$Cl$_2$/EtOAc (3:1 to 1:1)) to give the title compound.

EXAMPLE 8

Step 1

3,5-Bis(tetra-O-acetyl-β-D-glucosyloxymethyl)-1-nitrobenzene

The title compound was prepared by the procedure described in step 1 of Example 1 using 1 equivalent of 5-nitro-m-xylene-α,α'-diol, two equivalents of acetobromoglucose, and two equivalents of all other reagents. Purification was achieved by flash chromatography (EtOAc/CH$_2$Cl$_2$ (1:4 to 1:2) to give a 29% yield of nearly pure title compound which was used without further purification.

Step 2

3,5-Bis(tetra-O-acetyl-β-D-glucosyloxymethyl) phenylamine

The title compound was prepared by procedure A of step 2 of Example 1 using 6.27 g of 3,5-bis-(tetra-O-acetyl-β-D-glucosyloxymethyl)-1-nitrobenzene. Purification was achieved by flash chromatography (CH$_2$Cl$_2$/EtOAc (3:2)) to give 2.00 g (39% yield) of the title compound as a yellow oil: partial 1H-NMR (CDCl$_3$, 300 MHz) δ6.56 (s, 3 H), 5.0–5.2 (m, 6 H), 4.8 (d, 2 H), 4.4–4.6 (m, 4 H), 3.7 ppm (brd, 2 H).

EXAMPLE 9

Step 1

3,5-Bis(hepta-O-acetyl-β-maltosyloxymethyl)-1-nitrobenzene

The title compound was prepared by the procedure described in step 1 of Example 1 using 2.57 g (14.02 mmol; 1 equivalent) of 5-nitro-m-xylene-α,α'-diol, two equivalents of acetobromomaltose, and two equivalents of all other reagents, all in CH$_3$NO$_2$ (200 mL). Purification was achieved by flash chromatography (EtOAc/CH$_2$Cl$_2$ (1:2 to 1:1). Rechromatography (Et$_2$O) gave 11.4 g (57% yield) of the title compound which was used in the next reaction: partial $^1$H-NMR (CDCl$_3$, 300 MHz) δ8.11 (s, 2 H), 7.49 (s, I H), 5.42 (d, 2 H), 5.36 (t, 2 H), 5.26 (t, 2 H), 5.06 (t, 2 H), 4.21–4.29 (m, 4 H), and 3.69–3.72 ppm (m, 2 H).

Step 2

3,5-Bis(hepta-O-acetyl-β-D-maltosyloxymethyl) phenylamine

The title compound was prepared by procedure A of step 2 of Example 1 using 3,5-bis(hepta-O-acetyl-β-D-maltosyloxymethyl)-1-nitrobenzene. Purification was achieved by flash chromatography (CH$_2$Cl$_2$/EtOAc (1:1)) to give 4.43 g (40% yield) of the title compound: partial $^1$H-NMR (CDCl$_3$, 300 MHz) δ6.57 (s, 3 H), 5.41 (d, 2 H), 5.36 (t, 2 H), 5.23 (t, 2 H), 5.50 (t, 2 H), 4.75 (d, 2 H), 4.26 (m, 4 H), and 3.65–3.69 ppm (m, 2 H).

EXAMPLE 10

Step 1

Dodecanedioic Acid Bis{[5-(β-D-cellobiosyloxymethyl)-2-methylnhenyllamide}

To a solution of 5-(hepta-O-acetyl-β-D-cellobiosyloxymethyl)-2-methylphenylamine (1.03 g, 1.36 mmol) and triethylamine (189 μL, 1.36 mmol) in THF (15 mL) was added dodecanedioyl dichloride (170 μL, 0.681 mmol). After stirring at room temperature for 2 h, the reaction mixture was quenched with MeOH, diluted with CH$_2$Cl$_2$, and then washed with water. The organic phase was dried (MgSO$_4$), filtered, and concentrated to give 1.157 g of a colorless solid. This product was dissolved in MeOH (25 mL) and was treated with 11.9 mL (11.9 mmol) of 1N NaOH. After stirring at 50° C. for 5 h, the reaction mixture was cooled to room temperature and treated with 9.5 mL (9.5 mmol) of 1N HCl. Collection of the colorless solid provided the title compound (566 mg, 75% yield), mp >200° C.: partial $^1$H (DMSO-d$_6$, 400 MHz) δ9.25 (s, 2 H), 7.32 (s, 2 H), 7.16 (d, 2 H), 7.10 (d, 1 H), 4.77 (d, 2 H), 4.50 (d, 2 H), 4.24–4.30 (two doublets, 2 H), 3.78 (d, 2 H), 3.69 (d, 2 H), 3.63 (br d, 2 H), 2.99 (t, 2 H), 2.30 (t, 4 H), 1.58 (br t, 4 H), and 1.29 ppm (br s, 12 H); $^{13}$C-NMR (DMSO-d$_6$, 100 MHz) δ171.1, 136.2, 135.5, 131.1,130.0, 124.8, 103.2, 101.7, 80.6, 76.8, 76.4, 75.0, 74.9, 73.3, 73.1, 70.0, 69.5, 61.0, 60.4, 35.7, 28.9, 28.8, 28.7, 25.3, and 17.6 ppm; mass spectrum (-FAB) m/z 1115 (M-H); IR (KBr) 3430 and 1660 cm$^{-1}$. Anal. Calcd. for C$_{52}$H$_{80}$N$_2$O$_{24}$4 H$_2$O: C, 52.51; H, 7.46; N, 2.36. Found: C, 52.53; H, 7.28; N, 2.27.

Step 2

Dodecanedioic Acid Bis{[2-methyl-5-(hepta-O-sulfato-β -D-cellobiosyloxymethyl)phenyl]amide} Tetradecasodium Salt A solution of dodecanedioic acid bis{[5-(β-D-cellobiosyloxymethyl)-2 -methyl-phenyl]amide} (391 mg, 0.350 mmol) and sulfur trioxide trimethylamine complex (3.66 g, 26.3 mmol) in DMF (40 mL) was heated a 70° C. for 3 days. The reaction mixture was concentrated in vacuo and passed through a Sephadex G-10 column (twice). Cation exchange was effected using a Dowex 50×8 strongly acidic (Na form) column to give 433 mg of the title compound: partial $^1$H-NMR (D$_2$O, 400 MHz) δ7.39 (d, 2 H), 7.36 (d, 2 H), 7.29 (s, 2 H), 4.94 (d, 2 H), 4.80–4.90 (m, 4 H), 4.59 (dd, 2 H), 2.49 (t, 4 H), 2.23 (s, 3 H), 2.30–2.40 (m, 4 H), and 1.30–1.50 ppm (m, 12 H); $^{13}$C-NMR (D$_2$O, 100 MHz) δ176.8, 135.2, 134.9, 134.4, 130.9, 127.8, 127.1, 100.0, 99.1, 77.7, 77.4, 77.1, 74.4, 73.7, 73,5, 73.1, 70.7, 67.7, 66.6, 35.8, 28.5, 28.3, 25.5, and 16.9 ppm; mass spectrum (negative electrospray) (m-zNa)/z 825.6 (M-3Na)$^{3-}$, 613,5 (M-4Na)$^{4-}$, and 486.2 (M-5Na)$^{5-}$. Anal. Calcd. for C$_{52}$H$_{66}$N$_2$O$_{66}$S$_{14}$Na$_{14}$.14 H$_2$: C, 17.83; H, 2.70; N, 0.80; S, 17.40. Found: C, 17.96; H, 2.57; N, 0.72; S, 17.11.

EXAMPLE 11

Step 1

N,N'-Bis[5-(β-cellobiosyloxymethyl)-2- methylphenyl]terephthalamide

To 813 mg (1.08 mmol) of 5-(hepta-O-acetyl-β-D-cellobiosyloxymethyl)-2-methylphenylamine in THF (20 mL) containing triethylamine (148 µL, 1.08 mmol) was added terephthaloyl chloride (109 mg, 0.538 mmol). After stirring at ambient temperature for 2 h, the reaction mixture was quenched with MeOH, diluted with CH$_2$Cl$_2$ and washed with water. Drying (MgSO$_4$) and concentration gave crude product, which was diluted with MeOH (25 mL) and treated with 8.7 mL (8.7 mmol) of 1N NaOH. After stirring at 50° C. for 3 h, the suspension was filtered to provide 512 mg (89%) yield of the title compound as a colorless solid, mp >210° C.: $^1$H (DMSO-d$_6$; 400 MHz) δ10.07 (s, 2 H), 8.10 (s, 4 H), 7.35 (s, 2 H), 7.26 (d, 2 H), 7.22 (d, 2 H), 5.22–5.24 (m, 4 H), 5.01 (d, 2 H), 4.99 (d, 2 H), 4.82 (d, 2 H), 4.68 (d, 2 H), 4.54–4.64 (m, 6 H), 4.32 (d, 2 H), 4.25 (d, 2 H), 3.75–3.80 (d, 2 H), 3.63– 3.77 (m, 4 H), 3.37–3.41 (m, 2 It), 2.97–3.19 (m, 10 H), and 2.23 ppm (s, 6 H); $^{13}$C-NMR DMSO-d$_6$; 100 MHz) δ164.6, 137.0, 136.0, 135.9, 133.0, 130.1,127.7, 126.0, 125.6, 103.2, 101.8, 80.6, 76.8, 76.4, 75.1, 74.9, 73.3, 73.2, 70.0, 69.3, 61.0, 60.4, and 17.7 ppm; mass spectrum m/z 1052, 889, and 725. Anal. Calcd. for C$_{48}$H$_{64}$N$_2$O$_{24}$: C, 54.75; H, 6.13; N, 2.66. Found: C, 55.54, H, 6.33; N, 2.57.

Step 2

N,N'-Bis[5-(hepta-O-sulfato-β-D- cellobiosyloxymethyl)-2 -methylphenyl]terephthalamide Tetradecasodium Salt A mixture of N,N'-bis[5-(β-cellobiosyloxymethyl)-2-methylphenyl]terephthalamide (321 mg, 0.305 mmol) and sulfur trioxide trimethylamine complex (3.06 g, 22.0 mmol) in DMF (25 mL) was stirred at 70° C. for 4 days. The reaction mixture was concentrated and passed through a Sephadex G-10 column. $^1$H-NMR analysis showed incomplete sulfation. The product was resubmitted to sulfation with 3.06 g (22.0 mmol) of sulfur trioxide trimethylamine complex in 25 mL of DMF at 70° C. for 5 days. The reaction mixture was cooled to ambient temperature, concentrated in vacuo, and passed through a Sephadex G-10 column. Cation exchange using a Dowex column (50×8; strongly acidic; Na form) provided 469 mg (62% yield) of the title compound, mp 178 ° C. (dec): partial $^1$H-NMR (D$_2$O; 400 MHz) δ8.11 (s, 4H), 7.40–7.50(m, 6H), 4.98(d, 2H), 4.95(d, 2H), and 2.32 ppm (s, 6 H); $^{13}$C-NMR (D$_2$O; 100 MHz) δ169.5, 136.9, 135.4, 135.2, 134.3, 131.0, 128.1, 128.0, 127.0, 100.0, 99.1, 77.7, 77.4, 77.3, 77.1, 74.4, 73.7, 73.4, 73.1, 70.7, 67.7, 66.7, and 16.8 ppm. Anal. Calcd. for C$_{48}$H$_{50}$N$_2$O$_{66}$S$_{14}$Na$_{14}$.10 H$_2$O: C, 20.58; H, 2.51; N, 1.00; S, 17.17. Found: C, 20.21; H, 2.84; N, 0.96; S, 17.34.

EXAMPLE 12

Step 1

Biphenyl-4,4'-dicarboxylic Acid Bis{[5-(β-D-cellobiosyloxymethyl)-2 -methylphenyl]amide}

To a solution of 887 mg( 1.18 mmol) of 5-(hepta-O-acetyl-β-D-cellobiosyloxymethyl)- 2-methylphenylamine and 162 µL (1.18 mmol) of triethylamine in THF (20 mL) was added 164 mg (0.588 mmol) of biphenyl 4,4'-dicarboxylic acid chloride. After stirring at room temperature for 4 h, the reaction mixture was quenched with MeOH, diluted with CH$_2$Cl$_2$ and washed with water. The organic phase was dried (MgSO$_4$), filtered, and concentrated to a colorless solid (1.01 g). A solution of the crude material (985 mg, 0.574 mmol) in MeOH (25 mL) containing 9.18 mL (9.18 mmol) of 1N NaOH was stirred for 3 h at 50° C. The reaction mixture was cooled, and title compound was collected as a white powder (444 mg, 69% yield): partial $^1$H-NMR (DMSO-d$_6$; 300 MHz) δ10.01 (s, 2 H), 8.13 (d, 4 H), 7.94 (d, 4 H), 7.37 (s, 2 H), 7.28 (d, 2 H), 7.23 (d, 2 H), 5.24 (d, 2 H), 5.00 (q, 2 H), 4.84 (d, 2 H), 4.56–4.69 (m, 4 H), 4.33 (d, 2 H), 4.27 (d, 2 H), and 2.25 ppm (s, 3 H).

Step 2

Biphenyl-4,4'-dicarboxylic Acid Bis{[5-(hepta-O-sulfato-β-D-cellobiosyloxymethyl)-2-methylphenyl]amide} Tetradecasodium Salt A solution of 437 mg (0.387 mmol) of biphenyl-4,4'-dicarboxylic acid bis{[5-β-D-cellobiosyloxymethyl)-2-methylphenyl]amide} and 3.85 g (27.7 mmol) of sulfur trioxide trimethylamine complex in DMF (25 mL) was stirred at 70° C. for 5 days. The reaction mixture was quenched with water and concentrated in vacuo. The residue was dissolved in a small amount of water and passed through a Sephadex G-10 column. Cation exchange was accomplished using Dowex 50×8 strongly acidic (Na form) resin to provide, after azeotropic drying with toluene, 742 mg (75% yield) of the title compound, mp 170° C. (dec): partial $^1$H-NMR (D$_2$O; 400 MHz) δ5 8.09 (d, 4 H), 7.97 (d, 4 H), 7.40 (m, 6 H), 4.98 (d, 2 H), 4.94 (d, 2 H), 4.63–4.68 (m, 4 H), 4.56 (dd, 2 H), 4.41 (dd, 2 H), 4.30–4.37 (m, 6 H), 4.17–4.23 (m, 4 H), 3.99–4.05 (m, 4 H), and 2.31 ppm (s, 6 H); $^{13}$C-NMR (D$_2$O; 100 MHz) δ169.7, 143.2, 135.3, 135.2, 134.4, 132.8, 130.9, 128.1, 128.0, 127.4, 127.0, 99.9, 98.9, 77.6, 77.3, 77.2, 77.0, 74.2, 73.6, 73.3, 73.0, 70.6, 67.6, 66.6, and 16.7 ppm. Anal. Calcd. for C$_{59}$H$_{54}$N$_2$O$_{66}$S$_{14}$Na$_{14}$.14 H$_2$O: C, 21.97; H, 2.80; N, 0.95; S, 16.29. Found: C, 21.77; H, 2.90; N, 0.95; S, 13.66.

EXAMPLE 13

Step 1

N,N'-Bis[5-(β-D-cellobiosyloxymethyl)-2-methylphenyl]isophthalamide

To a solution of 887 mg (1.18 mmol) of 5-(hepta-O-acetyl-β-D-cellobiosyloxymethyl)-2-methylphenylamine in THF (20 mL) containing triethylamine (162 μL, 1.18 mmol) was added isophthaloyl dichloride (119 mg, 0.587 mmol). After stirring at ambient temperature for 2 h, the reaction mixture was quenched with MeOH, diluted with CH$_2$Cl$_2$, and washed with water. The organic phase was dried (MgSO$_4$) and concentrated to give 1.00 g of a colorless solid. A solution of the crude product in MeOH (25 mL) containing 9.76 mL (9.76 mmol) of 1N NaOH was stirred at 50° C. for 3 h. The resulting solid was collected and azeotropically dried over toluene to give 355 mg (55% yield) of the title compound as a colorless powder, mp 200°–203° C.: partial $^1$H-NMR (DMSO-d$_6$; 400 MHz) δ10.09 (s, 2 H), 8.54 (s, 1 H), 8.15 (d, 2 H), 7.68 (t, 1 H), 7.34 (s, 2 H), 7.26 (d, 2 H), 7.21 (d, 2 H), 5.24 (t, 4 H), 5.01 (dd, 2 H), 4.82 (d, 2 H), 4.69 (s, 2 H), 4.54–4.69 (m, 4 H), 4.32 (d, 2 H), 4.25 (d, 2 H), 3.76–3.80 (m, 2 H), 3.63–3.69 (m, 4 H), and 2.24 ppm (s, 6 H); $^{13}$C-NMR (DMSO-d$_6$; 100 MHz) δ164.9, 136.1, 135.9, 134.8, 133.0, 130.5, 130.1, 128.6, 127.1, 125.9, 125.6, 103.2, 101.8, 80.6, 76.8, 76.4, 75.1, 74.9, 73.3, 73.2, 70.0, 69.4, 61.0, 60.4, and 17.7 ppm; mass spectrum (-FAB) m/z 1051, 727, and 889. Anal. Calcd. for C$_{48}$H$_{64}$N$_2$O$_{24}$.3 H$_2$O: C, 52.08; H, 6.37; N, 2.53. Found: C, 51.89; H, 6.31; N, 2.26.

Step 2

N,N'-Bis[5-(hepta-O-sulfato-β-cellobiosyloxymethyl)-2-methylphenyl]isophthalamide Tetradecasodium Salt A solution of N,N'-bis[5-(β-D-cellobiosyloxymethyl)-2-methylphenyl]isophthalamide (180 mg, 0.171 mmol) and 1.79 g (11.98 mmol) of sulfur trioxide trimethylamine complex in DMF (25 mL) was stirred at 70° C. for 4 days. The reaction mixture was concentrated and then purified using a Sephadex G-10 column with water elution. Cation exchange was effected with a column of Dowex 50×8 strongly acidic (Na form) resin with water elution. Removal of water in vacuo and azeotropic drying with toluene gave 358 mg (84% yield) of the title compound as a colorless solid, mp 171° C. (dec): partial $^1$H-NMR (D$_2$O; 400 MHz) δ8.43 (s, 2 H), 8.21 (dd, 2 H), 7.78 (t, 1 H), 7.40–7.50 (m, 6 H), 4.97 (d, 2 H), 4.94 (d, 2 H), 4.56 (dd, 2 H), and 2.30 ppm (s, 6 H); $^{13}$C-NMR (D$_2$O; 100 MHz) δ169.2, 135.3, 135.1, 134.3, 134.0, 131.0, 130.9, 129.3, 128.0, 126.9, 126.5, 99.9, 99.0, 135.5, 77.3, 77.2, 77.0, 74.3, 73.6, 73.3, 73.0, 70.6, 67.6, 66.6, and 16.7 ppm. Anal. Calcd. for C$_{48}$H$_{50}$N$_2$O$_{66}$S$_{14}$Na$_{14}$.14 H$_2$O.Na$_2$SO$_4$: C, 19.12, H, 2.61; N, 0.93; S, 17.01. Found: C, 18.97; H, 2.45; N, 0.94; S, 15.68.

EXAMPLE 14

Decanedioic Acid Bis{[3,5-bis(β-D-cellobiosyloxymethyl)phenyl]amide}

To a solution of 3,5-bis(hepta-O-acetyl-β-D-cellobiosyloxymethyl)phenylamine (817 mg, 0.588 mmol) and triethylamine (82 μL, 0.59 mmol) in THF (25 mL) was added 74 μL (0.295 mmol) of dodecanedioyl dichloride. The reaction mixture was stirred at ambient temperature for 90 min, quenched with MeOH, diluted with CH$_2$Cl$_2$, and washed with water. The organic phase was dried (MgSO$_4$) and concentrated to a colorless solid. (834 mg, 95% yield). The crude product was dissolved in MeOH (25 mL) and was treated with 8.4 mL (8.4 mmol) of 1N NaOH. After stirring at 50° C. for 2 h, the reaction mixture was quenched at room temperature with 7.84 mL of 1N HCl, concentrated, and purified by reverse phase column chromatography (RP silica 60) using MeOH/H$_2$O (1:1) elution. Rechromatography using MeOH/H$_2$O (2:3) provided 438 mg (87% yield) of the title compound as a colorless solid: partial $^1$H-NMR (D$_2$O; 400 MHz) δ7.45 (s, 4 H), 7.26 (s, 2 H), 4.64 (d, 4 H), 4.47 (t, 8 H), 3.80 (dd, 4 H), 3.71 (dd, 4 H), 2.30 (br t, 4 H), 1.55 (t, 4 H), and 1.17 ppm (br m, 12 H); $^{13}$C-NMR (D$_2$O; 100 MHz) δ175.1, 138.1, 137.7, 124.4, 120.3, 102.5, 101.3, 78.7, 75.9, 75.5, 74.7, 74.3, 73.1, 72.8, 70.8, 69.4, 60.5, 60.0, 36.6, 28.7, 28.6, 28.5, and 25.3 ppm. Anal. Calcd. for C$_{76}$H$_{120}$H$_2$O$_{46}$.10 H$_2$O: C, 46.15; H, 7.13; N, 1.42. Found: C, 45.91; H, 6.82; N, 1.41.

Step 2

Decanedioic Acid Bis{[3,5-bis(hepta-O-sulfato-β-D-cellobiosyloxymethyl}phenyl]amide} Octacosasodium Salt A solution of decanedioic acid bis{[3,5-bis(β-D-cellobiosyloxymethyl)phenyl]amide (177 mg, 98.4 mmol) and sulfur trioxide trimethylamine complex (1.97 g, 14.2 mmol) in DMF (25 mL) was stirred at 70° C. for 25 h. The reaction mixture was concentrated and purified by chromatography with Sephadex G-10 using water elution. Cation exchange using a column of Dowex 50×8 strongly acidic resin (Na form) provided 292 mg (64% yield) after azeotropic drying with toluene: partial $^1$H-NMR (D$_2$O; 400 MHz) δ7.55 (s, 4 ti), 7.35 (s, 2 H), 4.96–4.98 (m, 8 H), 2.45 (br t, 4 H), 1.40–1.60 (br t, 4 H), and 1.36–1.41 ppm (br m, 12 H); $^{13}$C-NMR (D$_2$O; 100 MHz) δ176.1, 138.0, 137.1, 124.5, 121.0, 99.9, 99.6, 77.6, 77.43, 77.39, 77.0, 74.3, 73.4, 72.9, 70.9, 67.6, 66.3, 36.5, 28.7, 28.5, and 25.3 ppm. Anal. Calcd.

for $C_{76}H_{92}N_2O_{30}\cdot 3$ $Na_2SO_4\cdot 28$ $H_2O$: C, 16.34; H, 2.67; N. 0.50; S, 17.8. Found: C, 16.25; H, 2.63; H, 0.59; S, 17.07.

EXAMPLE 15

Step 1

Biphenyl-4,4'-dicarboxylic Acid Bis{[3,5-bis(β-D-cellobiosyloxymehyl)phenyl]amide}

To a solution of 3,5-bis(hepta-O-acetyl-β-D-cellobiosyloxymethyl)phenylamine (817 mg, 0.588 mmol) and triethylamine (86 μL, 0.62 mmol) in THF (25 mL) was added 4,4-biphenyldicarboxylic acid dichloride (86 mg, 0.309 mmol). After stirring at room temperature for 2 h, the reaction n-fixture was quenched with MeOH, diluted with $CH_2Cl_2$, and washed with $H_2O$. The reaction mixture was dried ($MgSO_4$) and concentrated to give 921 mg of crude product, which was dissolved in MeOH (20 mL) and treated with 9.3 mL of 1N NaOH. After stirring at 50° C. for 4 h, 8.6 mL (8.6 mmol) of 1N HCl was added to the cooled reaction mixture. Collection of the solid provided 482 mg (86% yield) of the title compound: partial $^1$H-NMR (DMSO-$d_6$; 400 MHz) δ10.40 (s, 2 H), 8.11 (d, 4 H), 7.93 (d, 4 H), 7.74 (s, 4 H), 7.18 (s, 2 H), 4.86 (d, 4 H), 4.56 (d, 4 H), 4.35 (d, 4 H), 4.27 (d, 4 H), 3.80 (d, 4 H), and 2.97–3.07 ppm (m, 4 H); $^{13}$C-NMR (DMSO-$d_6$, 100 MHz) δ165.0, 142.0, 138.9, 138.2, 134.1, 128.5, 126.9, 122.8, 119.3, 103.2, 102.0, 80.5, 76.8, 76.5, 75.1, 75.0, 73.3, 73.2, 70.02, 69.96, 61.0, and 60.4 ppm; IR (KBr) 1650 cm$^{-1}$. Anal. Calcd. for $C_{78}H_{108}N_2O_{46}\cdot 10$ $H_2O$: C, 47.08; H, 6.48; N, 1.41. Found: C, 46.64; H, 6.22; N, 1.62.

Step 2

Biphenyl-4,4'-dicarboxylic Acid Bis{[3,5-bis(hepta-O-sulfato-β-D-cellobiosyloxymethyl)phenyl]amide} Octacosasodium Salt A solution of 338 mg (0.187 mmol) of biphenyl-4,4'-dicarboxylic acid bis{[3,5-bis(β-D-cellobiosyloxymethyl)phenyl]amide} and 3.64 g (26.1 mmol) of sulfur trioxide trimethylamine complex in DMF (25 mL) was stirred at 70° C. for 2 days. The reaction mixture was cooled to ambient temperature, quenched with water, and concentrated. Purification was achieved with a Sephadex G-10 column ($H_2O$ elution). Cation exchange was accomplished by passing an aqueous solution of the product through a column of Dowex 50×8 strongly acidic (Na form) resin. Removal of solvent and azeotropic drying with toluene gave 765 mg (88% yield) of the title compound as an off-white solid, mp 180° C. (dec): partial $^1$H-NMR (D$_2$O; 400 MHz) δ8.08 (d, 4 H), 7.97 (d, 4 H), 7.70 (s, 4 It), 7.39 (s, 2 H), 5.02 (d, 4 H), 4.98 (d, 4 H), 4.15–4.23 (m, 8H), and 4.00 ppm (m, 8 H); $^{13}$C-NMR (D$_2$O, 100 MHz) δ169.2, 143.3, 138.2, 137.3, 133,5, 128.3, 127.5, 125.0, 121.8, 100.0, 99.7, 77.7, 77.54, 77.51, 77.1, 74.4, 73,5, 73.0, 71.0, 67.7, and 66.4 ppm; mass spectrum (electrospray) (m-zNa)/z 401.3 (m—11 Na)$^{11-}$, 443.7 (m—10 Na)$^{10-}$, 495.6 (m—9 Na)$^{9-}$, 560.4 (m— 8 Na)$^{8-}$, and 643.7 (m—7 Na)$^{7-}$. Anal. Calcd. for $C_{78}H_{80}N_2O_{130}S_{28}Na_{28}\cdot 2$ $Na_2SO_4\cdot 28H_2O$: C, 17.17, H, 2.51; N, 0.51; S, 16.46. Found: C, 17.06; H, 211; N, 0.55; S, 12.04.

EXAMPLE 16

Step 1

Biphenyl-4,4'-dicarboxylic Acid Bis{[3,5-Bis(hepta-O-acetyl-β-D-lactosyloxymethyl)phenyl]amide)

To a solution of 3,5-bis(hepta-O-acetyl-β-D-lactosyloxymethyl)phenylamine (1.05 g, 0.757 mmol) and triethylamine (105 μL, 0.757 mmol) in THF (20 mL) was added 4,4-biphenyldicarboxylic acid dichloride (106 mg, 0.378 mmol). After stirring at room temperature for 2 h, the reaction mixture was quenched with MeOH, diluted with $CH_2Cl_2$, and washed with $H_2O$. The reaction mixture was dried ($MgSO_4$), concentrated, and purified by trituration from $CH_2Cl_2$/$Et_2O$ to give 984 mg (87% yield) of the title compound as a colorless solid, mp 163°–167° C.: $^1$H (CDCl$_3$; 400 MHz) δ8.62 (s, 2 H). 8.05 (d, 4 H), 7.74 (d, 4 H), 7.66 (s, 4 H), 6.93 (s, 2 H), 5.33 (d, 2 H), 5.17 (t, 2 H), 5.07–5.12 (m, 2 H), 4.91–4.97 (m, 4 H), 4.79 (d, 2 H), 4.62–4.66 (m, 4 H), 4.57 (d, 2 H), 4.51 (d, 2 H), 4.03–4.15 (m, 6 H), 3.80–3.88 (m, 4 H), 3.62 (dq, 2 H), 2.13 (s, 12 H), 2.10 (s, 12 H), 2.03 (s, 24 H), 2.02 (12 H), and 1.95 ppm (s, 12 H); mass spectrum (electrospray, Ca$^{2+}$ adduct) m/z 1513.2 (m+Ca)$^{2+}$. Anal. Calcd. for $C_{134}H_{164}N_2O_{74}\cdot 1$ $H_2O$: C, 53,56; H, 5.57; N, 0.93. Found: C, 53.25; H, 5.55; N, 1.06.

Step 2

Biphenyl-4,4'-dicarboxylic Acid Bis{[3,5-bis(hepta-O-sulfato-β-D-lactosyloxymethyl)phenyl]amide}Octacosasodium Salt A solution of 871 mg (0.292 mmol) of biphenyl-4,4'-dicarboxylic acid bis{[3,5-bis(hepta-O-acetyl-β-D-lactosyloxymethyl)phenyl]amide}in MeOH (15 mL) containing 8.75 mL of 1N NaOH (8.75 mmol) was stirred at 50° C. for 3 h. The reaction mixture was cooled to ambient temperature and was quenched with 8.16 mL (8.16 mmol) of 1N HCl. The resulting solid was collected and azeotropically dried with toluene: $^{13}$C-NMR (DMSO-$d_6$; 100 MHz) δ164.9, 141.9, 138.9, 138.2, 134.1, 128.4, 126.8, 119.2, 103.8, 101.9, 80.7, 75.5, 74.99, 74.96, 73.3, 73.2, 70.6, 69.9, 68.0, 60.5, and 60.3 ppm.

A solution of 396 mg (0.219 mmol) of biphenyl-4,4'-dicarboxylic acid bis{[3,5-bis-(β-D-lactosyloxymethyl)phenyl]amide} and 4.26 g (30.6 mmol) of sulfur trioxide timethylamine complex in DMF (20 mL) was stirred at 70° C. for 3 days. The reaction mixture was cooled to ambient temperature, quenched with distilled $H_2O$, and concentrated. The residue was purified by passing through a Sephadex G-10 column ($H_2O$ elution). Cation exchange was accomplished by passing an aqueous solution of the product through a column of Dowex 50×8 strongly acidic (Na form) resin. Removal of solvent and azeotropic drying with toluene gave 664 mg (65%) of a shiny white solid, mp 149° C. (dec): $^{13}$C-NMR (D$_2$O; 100 MHz) δ169.1, 143.1, 138.1, 137.3, 133.4, 128.2, 127.4, 124.9, 121.7, 100.9, 99.4, 77.6, 77.0, 75.8, 75.3, 75.05, 75.00, 73.0, 71.1, and 66.34 ppm; mass spectrum (electrospray) (m-zNa)/z 643.7 (m—7 Na)$^{7-}$, 754.8 (m—6 Na)$^{6-}$ and 910.4 (m - 5 Na)$^{5-}$. Anal. Calcd. for $C_{78}H_{80}N_2O_{130}S_{28}Na_{28}\cdot 28$ $H_2O$: C, 18.12; H, 2.65; N, 0.54; S, 17.36. Found: C, 18.06; H, 2.67; N, 0.50; S, 14.75. (NMR and capillary electrophoresis show one major component and several minor components; mass spectrum analysis indicates products from 20–28 sulfates).

EXAMPLE 7

Step 1

Biphenyl-4,4'-dicarboxylic Acid Bis[3,5-bis(tetra-O-acetyl-β-D-glucosyloxymethyl)phenyl]amide}

To a solution of 3,5-bis(tetra-O-acetyl-β-D-glucosyloxymethyl)phenylamine (996 mg, 1.22 mmol) and triethylamine (160 μL, 1.22 mmol) in THF (15 mL) was added 4,4'-biphenyldicarboxylic acid dichloride (171 mg, 0.612 mmol). After stirring at room temperature for 3 h, the reaction mixture was quenched with MeOH, diluted with $CH_2Cl_2$, and washed with $H_2O$. The reaction mixture was dried ($MgSO_4$), concentrated, and purified by trituration from $CH_2Cl_2/Et_2O$ to give 984 mg (87% yield) of the title compound as a colorless solid, mp 125°–130° C.: $^1$H (CDCl$_3$; 400 MHz) δ8.42 (s, 12 H), 8.04 (d, 4 H), 7.75 (d, 4 H), 7.66 (s, 4 H), 6.98 (s, 2 H), 5.03– 5.22 (m, 12 H), 4.85 (d, 4 H), 4.67 (d, 4 H), 4.61 (d, 4 H), 4.22–4.32 (m, 8 H), 3.72 (dq, 4 H), 2.06 (s, 12 H), 2.024 (s, 12 It), 2.019 s, 12 H), and 1.99 ppm (s, 12 H); mass spec ((–)-FAB), m/z 1159 (MAD. Anal. Calcd. for $C_{54}H_{68}N_2O_{26}.6H_2O$: C, 51.10; H, 6.35; N, 2.21. Found: C, 51.01; H, 6.09; N, 2.25.

Step 2

Biphenyl-4,4'-dicarboxylic Acid Bis{[3,5-bis(β-D-glucosyloxymethyl}phenyl]amide}

A solution of 575 mg (0.495 mmol) of biphenyl-4,4'-dicarboxylic acid bis{[3,5-bis-(tetra-O-acetyl-β-D-glucosyloxymethyl)phenyl]amide} and 8.91 mL (8.9 mmol) of 1N NaOH in MeOH (15 mL) was stirred at 50° C. for 4 h. The reaction mixture was quenched with 1N HCl (7.9 mL) and purified by Sephadex G-10 chromatography ($H_2O$ elution). Removal of $H_2O$ in vacuo gave 144 mg (25% yield) of the title compound, mp 160° C. (dec): $^1$H ($D_2O$; 400 MHz) δ5 7.38 (d, 4 H), 7.20 (s, 4 H), 7.16 (d, 4 H), 7.07 (s, 2 H), 4.72 (d, 4 H), 4.47 (d, 4 H), 4.38 (d, 4 H), 3.88 (d, 4 H), 3.69 (dd, 4 H), and 3.27–3.44 ppm (m, 16 H); $^{13}$C-NMR ($D_2O$; 100 MHz) δ 166.3, 141.6, 137.6, 137.2, 131.7, 127.5, 126.3, 124.0, 120.1, 101.5, 75.7, 75.6, 73.0, 70.7, 69.5, and 60.6 ppm; mass spectrum ((–)-FAB) m/z 1159.4 (M - H), 997.3, 981.3, and 699.2. Anal. Calcd. for $C_{54}H_{68}N_2O_{26}.6H_2O$: C, 51.10; H, 6.35; N, 2.21. Found: C, 51.01; H, 6.09; N, 2.25.

Step 3

Biphenyl-4,4'-dicarboxylic Acid Bis{[3,5-bis(tetra-O-sulfato-β-D-glucosyloxymethyl)phenyl]amide}Hexadecasodium Salt A solution of 92 mg (0.079 mmol) of biphenyl-4,4'-dicarboxylic acid bis{[3,5 -bis(β-D-glucosyloxymethyl)phenyl]amide} and 450 mg (6.83 mmol) of sulfur trioxide trimethylamine complex in DMF (15 mL) was stirred at 70° C. for 3 days. The reaction mixture was cooled to ambient temperature, quenched with distilled $H_2O$, and concentrated. The residue was purified by passing through a Sephadex G-10 column ($H_2O$ elution). Cation exchange was accomplished by passing an aqueous solution of the product through a column of Dowex 50×8 strongly acidic (Na form) resin. Removal of solvent and azeotropic drying with toluene gave 161 mg (73%) of a shiny white solid, mp 172° C. (dec): $^1$H-NMR ($D_2O$; 400 MHz) δ8.10 (dd, 4 H), 7.97 (dd, 4 H), 7.71 (s, 4 H), 7.40 (s, 2 H), 5.05 (d, 4 H), 5.01 (dd, 4 H), 4.89 (d, 4 H), 4.47– 4.60 (m, 12 H), 4.28 (dt, 4 H), and 4.19–4.22 ppm (m, 4 H); $^{13}$C-NMR ($D_2O$; 100 MHz) δ169.1, 143.1, 138.0, 137.3, 133.4, 128.2, 127.3, 125.0, 121.8, 99.3, 76.0, 75.7, 73.4, 72.5, 70.8, and 67.7 ppm. Anal. Calcd. for $C_{54}H_{52}N_2O_{74}S_{16}N_{16}.16.H_2O$: C, 21.01; H, 2.75; N, 0.91; S, 16.65. Found: C, 20.93; H, 2.78; N, 0.77; S, 16.86. Capillary electrophoresis shows purity in excess of 91%.

EXAMPLE 18

Step 1

Biphenyl-4,4'-dicarboxylic Acid Bis([3,5-bis(hepta-O-acetyl-β-D-maltosyloxymethyl)phenyl]amide}

To a solution of 3,5-bis(hepta-O-acetyl-β-D-maltosyloxymethyl)phenylamine (1.07 g, 0.769 mmol) and triethylamine (101 μL, 0.769 mmol) in THF (20 mL) was added 4,4'-biphenyldicarboxylic acid dichloride (107 mg, 0.385 mmol). After stirring at room temperature for 3 h, the reaction mixture was quenched with MeOH, diluted with $CH_2Cl_2$, and washed with $H_2O$. The reaction mixture was dried ($MgSO_4$) and concentrated to give 1.10 g (96% yield) of the title compound as a colorless solid, mp 139°–144° C.: $^1$H-NMR (CDCl$_3$, 400 MHz) δ8.66 (bs, 2 H), 8.03 (d, 4 H), 7.72 (d, 4 H), 7.67 (s, 4 H), 6.93 (s, 2 H), 5.39 (d, 4 H), 5.32 (t, 4 H), 5.20 (t, 4 H), 5.02 (t, 4 H), 4.76–4.86 (m, 12 H), 4.57–4.66 (m, 12 H), 4.20–4.25 (m, 8 H), 3.93–4.04 (m, 12 H), 3.6–3.7 (m, 4 H), 2.09 (s, 12 H), 2.06 (s, 12 H), 1.99 (s, 12 H), 1.98 (s, 12 H), 1.97 (s, 12 H), 1.96 (s, 12 H), and 1.95 ppm (s, 12 H); IR (KBr)1745 cm$^{-1}$. Anal. Calcd. for $C_{134}H_{164}N_2O_{74}$: C, 53.89; H, 5.53; N, 0.94. Found: C, 53.49; H, 5.55; N, 0.94.

Step 2

Biphenyl-4,4'-dicarboxylic Acid Bis{[3,5-bis(β-D-maltosyloxymethyl)phenyl]amide}

A solution of 973 mg (0.326 mmol) of biphenyl-4,4'-dicarboxylic acid bis{[3,5-bis(hepta-O-acetyl-β-D-maltosyloxymethyl)phenyl]amide}and 9.77 mL (9.77 mmol) of 1N NaOH in MeOH (15 mL) was stirred at 50° C. for 4 h. The reaction mixture was cooled to room temperature, quenched with 1N HCl (9.12 mL), concentrated, and purified by Sephadex G-10 chromatography ($H_2O$ elution). Removal of $H_2O$ in vacuo gave 494 mg (75% yield) of the title compound, mp >200° C.: $^1$H-NMR ($D_2O$, 400 MHz) δ7.54 (s, 4 H), 7.33 (s, 4 H), 7.23–7.27 (br, 4 H), 7.15 (s, 2 H), 5.32 (s, 4 H), 4.51–4.20 (brd 4 H), 4.39 (d, 4 H), 3.50–3.90 (m, 36 H), and 3.30–3.45 ppm (m, 12 H); $^{13}$C-NMR (D20; 100 MHz) δ166.3, 141/7, 137.8, 137.3, 132.0, 127.7, 126.5, 124.1, 120.1, 101.3, 99.9, 77.4, 75.9, 74.4, 72.8, 72.6, 71.6, 70.6, 69.1, 60.6, and 60.3 ppm. Anal. Calcd. for $C_{78}H_{108}N_2O_{46}.8H_2O$: C, 48.85; H, 6.31; N, 1.46. Found: C, 48.48; H, 6.28; N, 1.58.

Step 3

Biphenyl-4,4'-dicarboxylic Acid Bis{[3,5-bis(hepta-O-sulfato β-D-maltosyloxymethyl)}phenyl]amide}Octacosasodium Salt A solution of 315 mg (0.174 mmol) of biphenyl-4,4'-dicarboxylic acid bis{[3,5-bis(β-D-maltosyloxymethyl)phenyl]amide} and 3,58 g, (25.7 mmol) of sulfur trioxide trimethylamine complex in DMF (15 mL) was stirred at 70° C. for 3 days. The reaction mixture was cooled to ambient temperature, quenched with distilled $H_2O$, and concentrated. The residue was purified by passing through a Sephadex G-10 column ($H_2O$ elution). Cation exchange was accomplished by passing an aqueous solution of the product through a column of Dowex 50×8 strongly acidic (Na form) resin. Removal of solvent and azeotropic drying with toluene gave 609 mg (75%) of an off-white solid, mp 178° C. (dec): $^1$H-NMR ($D_2O$; 400 MHz) δ8.06 (d, 4 H), 7.94 (d, 4 H), 7.69 (s, 4 H), 7.36 (s, 2 H), 5.58 (d, 4 H), 5.06 (d, 4 H), 5.02 (d, 4 H), 4.7–4.9 (m, 12 H), 4.58–4.61 (m, 8 H), 4.49 (dd, 4 H), 4.12–4.46 ppm (m, 28 H); $^{13}$C-NMR ($D_2O$; 100 MHz) δ169.1, 143.1, 138.0, 137.3, 133.4, 128.2, 127.4, 124.9, 121.7, 99.3, 94.1, 77.1, 76.0, 74.8, 73.2, 73.1, 72.3, 71.8, 70.5, 69.9, 67.5, and 66.0 ppm; mass spectrum (electrospray) (m-zNa)/z 1143.7 (m-4 Na)$^{4-}$, 910.4 (m-5 Na)$^{5-}$, 754.8 (m—6 Na6-), 643.7 (m—7 Na7-), 560.4 (m—8 Na)$^{8-}$. Calcd. for $C_{78}H_{80}N_2O_{130}S_{28}Na_{28}\cdot28H_2O$: C, 18.12; H, 2.65; N, 0.54; S, 17.36. Found: C, 18.33; H, 2.73; N, 0.46; S, 17.72.

EXAMPLE 19

Step 1

3,3'-(N,N'-Ureido)bis{N-[5-(hepta-O-acetyl-β-D-cellobiosyloxymethyl)-2-chlorophenyl]benzamide}

To a solution of 1.10 g (1.42 mmol) of 5-(hepta-O-acetyl-β-D-cellobiosyloxymethyl-2-chlorophenylamine in THF (20 mL) containing 198 μL (1.42 mmol) of triethylamine was added 3-nitrobenzoyl chloride (316 mg, 1.70 mmol). After 3 h, the reaction mixture was quenched with MeOH and diluted with $CH_2Cl_2$. The reaction mixture was washed with $H_2O$, dried ($MgSO_4$), filtered, and concentrated to 1.31 g (1.42 mmol) of crude product which was used directly in the next reaction. The crude material was dissolved in EtOAc and was treated with 2.32 g (10.28 mmol) of $SnCl_2\cdot H_2O$. After stirring at reflux for 5 h, the reaction mixture was cooled to room temperature and was quenched with sat. $NaHCO_3$ (300 mL). The reaction mixture was diluted with EtOAc, and filtered. The organic phase was separated and the aqueous phase was extracted with $CH_2Cl_2$. The organic phases were combined, dried ($MgSO_4$) and concentrated to give 1.18 g (93% yield) of crude product which was used directly in the next reaction. To the product in THF (20 mL) containing 108 μL (7.98 mmol) of pyridine was added 66 mg (0.22 mmol) of triphosgene. The mixture was stirred at ambient temperature overnight. The reaction mixture was quenched with $H_2O$ and then stirred for another 30 min. The reaction mixture was filtered. The solid was collected and dissolved in $CH_2Cl_2$, dried ($MgSO_4$), concentrated, and then triturated with $Et_2O$ to give 995 mg (82% yield) of the title compound, mp 173°–178° C.: $^1$H-NMR ($CDCl_3$, 400 MHz) δ8.47 (s, 2 H), 8.41 (d, 2 H), 7.45 (d, 2 H), 7.38 (t, 2 H), 7.33 (d, 2 H), 6.96 (dd, 2 H), 5.10–5.16 (m, 4 H), 5.03 (t, 2 H), 4.90- 4.96 (m, 4 H), 4.79 (d, 2 H), 4.59 (t, 2 H), 4.51–4.56 (m, 4 H), 4.30 (dd, 1 H), 4.14 (dd, 1 H), 3.99 (dd, 2 H), 3.92 (t, 2 H), 3.65–3.70 (dq, 2H), 2.09 (s, 6 H), 2.04 (s, 6 H), 2.02 (s, 12 H), 1.987 (s, 6 H), 1.985 (s, 6 H), and 1.96 ppm (s, 6 H); $^{13}$C-NMR ($CDCl_3$; 100 MHz) δ170.6, 170.49, 170.46, 169.83, 169.17, 169.14, 165.22, 152.47, 139.75, 136.78, 134.85, 134.43, 129.68, 129.13, 124.35, 123.08, 122.95, 121.18, 120.57, 117.99, 100.70, 98.92, 73.22, 72.64, 71.89, 71.74, 71.55, 71.49, 69.97, 67.90, 62.04, 61.53, 20.86, 20.72, 20.64, 20.58, 20.53, and 20.45 ppm; mass spectrum ((+)-FAB) m/z 1837.5 (M+Na). Anal. Calcd. for $C_{81}H_{92}N_4O_{39}Cl_2\cdot H_2O$: C, 53.03; H, 5.16; N, 3.05. Found: C, 52.74; H, 5.09; N, 3.15.

Step 2

3,3'-(N,N'-Ureido)bis{[N-[5-(β-D-cellobiosyloxymethyl)-2-chlorophenyl]benzamide}

A solution of 908 mg (0.50 mmol) of 3,3'-(N,N'-ureido)bis{N-[5-(hepta-O-acetyl-β-cellobiosyloxymethyl)-2-chlorophenyl]benzamide} in MeOH (20 mL) containing 7.5 mL (7.5 mmol) of 1N NaOH was stirred at 50° C. under $N_2$ for 4 h. The reaction mixture was cooled to room temperature and was quenched with 1N HCl (7.0 mL, 7.0 mmol). The reaction mixture was stirred for 15 min and filtered. The solid was collected and azeotropically dried with toluene to provide 566 mg (92% yield) of the title compound as an off-white solid, mp 183° C.: partial $^1$H-NMR (DMSO-$d_6$, 400 MHz) δ5 10.06 (s, 2 H), 9.28 (s, 2 H), (s, 1 H), 2 H), 7.75 (d, 1 H), 7.60 (d, 2 H), 7.59 (s, 2 H), 7.50–7.55 (q, 4 H), 7.44 (d, 2 H), 7.33 (dd, 2 H), 5.30 (s, 2 H), 5.25 (d, 2 H), 4.86 (d, 2 tt), 4.70 (s, 2 H), 4.33 (d, 2 H), 4.25 (d, 2 H), 3.75–3.80 (dd, 2 H), 3.60–3.71 (m, 4 H), and 3.0–3.2 ppm (m, 8 H); $^{13}$C-NMR (DMSO-$d_6$; 100 MHz) δ165.54, 152.70, 140.05, 137.74, 134.90, 134.78, 129.27, 128.95, 128.48, 127.36, 126.53, 121.58, 120.91, 117.80, 103.21, 101.99, 80.49, 76.79, 76.46, 75.01, 73.29, 73.19, 70.04, 68.82, 61.02, and 60.43 ppm; mass spectrum ((+)-FAB) m/z 1249.2 (M+Na). Anal. Calcd. for $C_{53}H_{64}N_4O_{25}Cl_2\cdot4H_2O$: C, 48.97; H, 5.58; N, 4.31. Found: C, 49.25; H, 5.58; N, 4.28.

Step 3

3,3'-(N,N'-Ureido)bis({N-[2-chloro-5-(hepta-O-sulfato-β-D-cellobiosyloxymethyl)phenyl]}benzamide) Tetradecasodium Salt To a solution of 3,3'-(N,N'-ureido)bis{N-[5-(β-cellobiosyloxymethyl)-2-chlorophenyl] benzamide} (475 mg, 0.387 mmol) in DMF (25 mL) containing 3.77 g (27.08 mmol) of sulfur trioxide trimethylamine complex was stirred at 70° C. for 3 days. The reaction mixture was cooled to room temperature, quenched with distilled $H_2O$, and concentrated. The residue was purified by passing through a Sephadex G-10 column ($H_2O$ elution). Cation exchange was accomplished by passing an aqueous solution of the product through a column of Dowex 50×8 strongly acidic (Na form) resin. Removal of solvent and azeotropic drying with toluene gave 926 mg (0.349 mmol) of the title compound as an off-white solid, mp 168° C. (dec): $^{13}$C-NMR ($D_2O$; 100 MHz) δ169.46, 155.29, 138.29, 136.85, 133.89, 133.06, 129.90, 129.63, 129.56, 128.43, 127.62, 124.74, 122.79, 119.59, 99.91, 99.14, 77.61, 77.32, 77.03, 74.28, 73.63, 73.34, 70.0, 67.60, and 66.60 ppm. Anal. Calcd. for $C_{53}H_{50}N_4O_{67}S_{14}Na_{14}\cdot3Na_2SO_4\cdot18H_2O$: C, 19.08; H, 2.60; N, 1.68; S, 16.34. Found: C, 19.01; H, 2.21; N, 1.74; S, 16.82. Capillary zone electrophoresis shows >90% purity.

EXAMPLE 20

Step 1

Biphenyl-4,4'-dicarboxylic Acid Bis{[2-chloro-5-(β-D-cellobiosyloxymethyl)phenyl]amide}

To a solution of 5-(hepta-O-acetyl-β-D-cellobiosyloxymethyl)-2-chlorophenylamine (995 mg, 1.28 mmol) and triethylamine (148 μL, 1.28 mmol) in THF (25 mL) was added 4,4'-biphenyldicarboxylic acid dichloride (179 mg, 0.642 mmol). After stirring at room temperature for 2 h, the reaction mixture was quenched with MeOH, diluted with $CH_2Cl_2$, and washed with $H_2O$. The reaction mixture was dried ($MgSO_4$) and concentrated to an oil which was triturated with ether to provide 1.09 g of crude product (99% yield). The material was dissolved in MeOH (20 mL) and treated with 9.5 mL of 1N NaOH. After stirring at 50° C. for 4 h, the reaction mixture was cooled to room temperature and treated with 8.9 mL (8.9 mmol) of 1N HCl. Collection of the solid provided 670 mg (91% yield) of the title compound, mp >200° C., after azeotropic drying with toluene: partial $^1$H-NMR (DMSO-$d_6$; 400 MHz) δ10.21 (s, 2 H), 8.13 (d, 4 H), 7.95 (d, 4 H), 7.61 (d, 2 H), 7.55 (d, 2 H), 7.35 (dd, 2 H), 5.29 (d, 2 H), 5.25–5.26 (br, 2 H), 4.87 (d, 2 H), 4.71 (s, 2 H), 4.34 (d, 2 H), 4.26 (d, 2 H), 3.78 (dd, 2 H), 3.15 (br d, 2 H), and 3.05 ppm (br t, 2 H); partial $^{13}$C-NMR (DMSO-$d_6$; 100 MHz) δ165.0, 128.5, 127.0, 103.2, 102.0, 80.5, 76.8, 76.4, 75.0, 73.3, 73.2, 70.0, 68.8, 61.0, and 60.4 ppm.; mass spectrum (-FAB) m/z 1166.9, 1004.9, and 842.9. Anal. Calcd. for $C_{52}H_{62}N_2O_{24}Cl_2.5 H_2O$: C, 49.57; H, 5.76; N, 2.22. Found: C, 49.81; H, 5.36; N, 2.14.

Step 2

Biphenyl-4,4'-dicarboxylic Acid
Bis{[2-chloro-5-(hepta-O-sulfato-β
-D-cellobiosyloxymethyl)phenyl]amide}
Tetradecasodium Salt A solution of 531 mg (0.454 mmol) of biphenyl-4,4'-dicarboxylic acid bis{[2 -chloro-5-(β-D-cellobiosyloxymethyl)phenyl]amide}and 4.42 g (31.8 mmol) of sulfur trioxide trimethylamine complex in DMF (25 mL) was stirred at 70° C. for 2 days. The reaction mixture was concentrated and purified by Sephadex G-10 chromatography using $H_2O$ elution. Cation exchange was effected using a column of Dowex 50×8 strongly acidic (Na form) with $H_2O$ elution. Removal of water in vacuo and azeotropic drying with toluene gave 705 mg (60%) of the title compound as a white solid, mp 165° C. (dec): partial $^1$H-NMR (DMSO-$d_6$; 400 MHz) δ8.10 (d, 4 H), 7.97 (d, 4 H), 7.66 (d, 2 Iq), 7.65 (d, 2 H), 7.52 (dd, 2 H), 4.99 (d, 2 H), 4.97 (d, 2 H), 4.58 (d, 2 H), and 4.00–4.06 ppm (m, 4 H); 13C-NMR ($D_2O$; 100 MHz) δ 169.8, 143,5, 137.0, 133.2, 132.6, 130.04, 130.01, 128.7, 128.3, 128.0, 127.5, 99.9, 99.2, 77.7, 77.4, 77.1, 74.3, 73.6, 73.4, 73.2, 67.7, and 66.6 ppm; mass spectrum (electrospray) (m-zNa)/z 496.7 (m—5Na)$^{5-}$, 626.6 (m-4Na)$^{4-}$, and 843.2 (m-3Na)$^{3-}$ Anal. Calcd. for $C_{52}H_{48}Cl_2N_2Na_{14}O_{66}S_{14}.16 H_2O$: C, 21.63; H, 2.79; N, 0.97; S, 15.55. Found: C, 21.24; H, 2.31; N, 0.93; S, 12.25.

EXAMPLE 21

Step 1

Biphenyl-4,4'-dicarboxylic Acid
Bis{[2-(β-D-cellobiosyloxymethyl)-4
-chlororphenyl]amide}

To a solution of 861 mg (1.11 rental) of 2-(hepta-O-acetyl-β -D-cellobiosyloxymethyl)-4-chlorophenylamine and triethylamine (155 μL, 1.11 mmol) in THF (20 mL) was added 4,4'-biphenyldicarboxylic acid dichloride (155 mg, 0.555 mmol). After stirring at ambient temperature for 2 h, the reaction mixture was quenched with MeOH, diluted with $CH_2Cl_2$ and washed with $H_2O$. The organic phase was dried ($MgSO_4$), filtered, and concentrated to give 975 mg of crude product. This material was dissolved in MeOH (15 mL) and was treated with 8.3 mL (8.3 mmol) of 1N NaOH. After stirring for 4 h at ambient temperature, the reaction mixture was quenched with 7.8 mL of 1N HCl and the solid was collected to provide 590 mg (91% yield) of the title compound as an off-white solid, mp >200° C.: partial $^1$H-NMR (DMSO-$d_6$; 400 MHz) δ9.95 (s, 2 H), 8.11 (d, 4 H), 7.93 (d, 4 H), 7.67 (d, 2 H), 7.62 (d, 2 H), 7.42 (dd, 2 H), 5.45 (d, 2 H), 4.91 (d, 2 H), 4.34 (d, 2 H), and 4.25 ppm (d, 2 H); partial $^{13}$C-NMR (DMSO-$d_6$; 100 MHz) δ164.9, 142.2, 134.6, 134.5, 133.4, 128.5, 127.0, 103.2, 101.7, 80.4, 80.2, 76.8, 76.4, 75.0, 74.9, 73.3, 70.0, 66.3, 61.0, and 60.3 ppm; IR (KBr) 1650 cm$^{-1}$; mass spectrum (-FAB) m/z 1167.3, 843.3, and 704.2. Anal. Calcd. for $C_{52}H_{62}Cl_2N_2O_{24}.4 H_2O$: C, 50.29; H, 5.68; N, 2.26. Found: C, 50.37; H, 5.38; N, 2.32.

Step 2

Biphenyl-4,4'-dicarboxylic Acid
Bis{[4-chloro-2-(hepta-O-sulfato-β
-D-cellobiosyloxymelhyl)phenyl]amide}
Tetradecasodium Salt A solution of 447 mg (0.382 mmol) of biphenyl-4,4-dicarboxylic acid bis{[2-(β-D-cellobiosyloxymethyl)-4-chlorophenyl]amide}and 3.85 g (27.7 mmol) of sulfur trioxide trimethylamine complex in DMF (25 mL) was stirred at 70° C. for 6 days. The reaction mixture was quenched at room temperature with $H_2O$, concentrated, and passed through a Sephadex G-10 column ($H_2O$ elution). Cation exchange was effected by passing an aqueous solution of the compound through a Dowex 50×8 strongly acidic (Na form) cation exchange column ($H_2O$ elution). Removal of solvent and azeotropic drying with toluene gave 666 mg (67% yield) of the title compound as an off-white solid, mp 172° C., which was ca. 70% pure as determined by capillary electrophoresis: partial $^1$H-NMR ($D_2O$; 400 MHz) δ8.10 (d, 4 H), 7.99 (d, 4 H), 7.74 (s, 2 H), 7.46–7.53 (br, 4 H), 4.95 (d, 2 H), and 4.90 ppm (d, 2 H); $^{13}$C-NMR ($D_2O$; 100 MHz) δ169.9, 143.4, 134.5, 133.4, 132.4, 129.7, 129.0, 128.7, 128.3, 127.6, 99.9, 98.8, 77.6, 77.4, 77.0, 74.3, 73,5, 73.4, 73.0, 67.6, 66.9, and 66.3 ppm. Anal. Calcd. for $C_{52}H_{48}Cl_2N_2Na_{14}O_{66}S_{14}.14 H_2O$: C, 21.92; H, 2.69; N, 0.98; S, 15.75. Found: C, 21.98; H, 2.63; N, 1.08; S, 16.05.

EXAMPLE 22

Step 1

N,N'-Bis[3,5-bis(β-D-cellobiosyloxymehyl)
phenyl]succinamide

To a solution of 840 mg (0.604 mmol) 3,5-bis(hepta-O-acetyl-β-D-cellobiosyloxymethyl)phenylamine and 86.4 μL (0.31 mmol) of triethylamine in THF (20 mL) was added succinyl chloride (34.2 μL, 0.31 mmol). After stirring at room temperature for 1 h, incomplete reaction was observed. Another 10 μL (0.09 mmol) of succinyl chloride was added. The reaction was stirred for another 15 min, quenched with MeOH, diluted with $CH_2Cl_2$, washed with $H_2O$, dried ($MgSO_4$), filtered, and concentrated. Trituration with $Et_2O$ gave a green solid which was semi-purified by flash chromatography (EtOAc) to give a yellow solid (633 mg, 75% yield). The compound was dissolved in MeOH and was treated with 6.6 mL of 1N NaOH (6.6 mmol). After stirring at 50° C. for 4 h, the reaction mixture was cooled to room temperature and to it was added strongly acidic Amberlite resin until neutral pH was obtained. After stirring for 5 min, the reaction mixture was filtered and concentrated to a yellow solid. Purification by reverse phase chromatography (RP-60 silica gel) using elution of MeOH: H$_2$O (3:7) and then by Sephadex G-10 chromatography (H$_2$O elution) gave 278 mg (94%) of the title compound as a yellow solid: partial $^1$H-NMR (D$_2$O; 400 MHz) δ7.48 (s, 4 H), 7.31 (s, 2 H), 4.91 (d, 4 H), 4.71 (d, 4 H), 4.52 (t, 8 H), 3.82 (dd, 4 H), 3.74 (dd, 4 H), 3.43 (d, 4 H), and 2.81 ppm (s, 4 H); $^{13}$C-NMR (D$_2$O; 100 MHz) δ173.3, 137.9, 137.3, 124.9, 120.9, 102.4, 101.0, 78.5, 75.8, 75.3, 74.6, 74.1, 73.0, 72.7, 70.7, 69.3, 60.4, 59.9, and 31.4 ppm.

Step 2

N,N'-Bis[3,5-bis(hepta-O-sulfato-β-D-cellobiosyloxymethyl)phenyl]succinamide Octacosasodium Salt A solution of 278 mg (0.208 mmol) of N,N'-bis[3,5-bis(β-D-cellobiosyloxymethyl)phenyl] succinamide and sulfur trioxide trimethylamine complex (4.23 g, 29.0 mmol) in DMF (20 mL) was stirred at 70° C. for 3 days. The reaction mixture was quenched at room temperature with H$_2$O and then concentrated. Purification by Sephadex G-10 chromatography (H$_2$O elution) and then cation exchange using Dowex 50×8 strongly acidic (Na form) resin gave 606 mg (64% yield) of the title compound as a tan solid, mp 168° C. (dec): partial $^1$H-NMR (D$_2$O; 400 MHz) δ7.58 (s, 4 H), 7.36 (s, 2 H), 4.00–5.00 (m, 64 H), and 2.87 ppm (s, 4 H); $^{13}$C-NMR (D$_2$O; 100 MHz) δ173.3, 138.0, 137.1, 124.4, 99.9, 99.7, 77.6, 77.4, 77.0, 74.3, 73.4, 72.9, 70.9, 67.6, 66.2, and 37.1 ppm; mass spectrum (electrospray) (m-zNa)/z 734.1 (m—Na)$^{6-}$, 885.5 (m-5Na)$^{5-}$, and 1112.7 (m-4Na)$^{4-}$ Anal. Calcd. for C$_{68}$H$_{76}$N$_2$O$_{130}$S$_{28}$Na$_{28}$.38 H$_2$O: C, 15.62; H, 2.93; N, 0.54; S, 17.18. Found: C, 15.24; H, 2.43; N, 0.75; S, 17.67.

EXAMPLE 23

Step 1

N,N'-Bis[3,5-bis(β-D-cellobiosyloxymethyl)phenyl] terephthalamide

To a solution of 3,5-bis(hepta-O-acetyl-β-D-cellobiosyloxymethyl)phenylamine (823 mg, 0.592 mmol) and triethylamine (82.5 μL, 0.592 mmol) in THF (15 mL) was added terephthaloyl chloride (60.1 mg, 0.296 mmol). After stirring at ambient temperature for 2 h, the reaction mixture was quenched with MeOH, diluted with CH$_2$Cl$_2$ and washed with H$_2$O. The organic phase was dried (MgSO$_4$), filtered, concentrated, and triturated with Et$_2$O to provide 845 mg (98%) of crude product. This was dissolved in MeOH (20 mL) and treated with 8.7 mL (8.7 mmol) of 1N NaOH. After stirring at 50° C. for 3 h, the reaction mixture was cooled to ambient temperature and 8.1 mL (8.1 mmol) of 1N HCl was added. The solid was collected and dried in vacuo to provide 295 mg (59% yield) of the title compound as a white solid, mp 185° C. (dec): partial $^1$H-NMR (DMSO-d$_6$ with 5 drops D$_2$O; 400 MHz) δ 8.01 (s, 4 H), 7.64 (s, 4 H), 7.18 (s, 2 H), 4.81 (d, 2 H), 4.56 (d, 2 H), 4.33 (d, 2 H), 4.26 (d, 2 H), and 3.77 ppm (d, 2 H); $^{13}$C-NMR (DMSO-d$_6$; 100 MHz) δ164.7, 138.7, 138.2, 137.7, 127.7, 122.9, 119.3, 103.2, 101.9, 80.5, 76.8, 76.4, 75.1, 75.0, 73.3, 73.2, 70.0, 69.9, 61.0, and 60.4 ppm; IR (KBr) 1650 cm$^{-1}$. Anal. Calcd. for C$_{72}$H$_{104}$N$_6$O$_{46}$12 H$_2$O: C, 44.35; H, 6.62; N, 1.44. Found: C, 44.05; N, 6.30; N, 1.41.

Step 2

N,N'-Bis[3,5-bis(hepta-O-sulfato-β-D-cellobiosyloxymethyl)phenyl]terephthalamide Octacosasodium Salt A solution of 178 mg (0.103 mmol) of N,N'-bis[3,5-bis(β-D-cellobiosyloxymethyl)phenyl] terephthalamide and sulfur trioxide trimethylamine complex (2.0 g, 14.4 mmol) in DMF (20 mL) was stirred at 70° C. for 3 days. The reaction mixture was cooled, quenched with water, and concentrated. The residue was purified by Sephadex G-10 chromatography (H$_2$O elution). Cation exchange was effected using a column of Dowex 50×8 strongly acidic (Na form) resin to afford 402 mg (85% yield) of the title compound as an off-white solid, mp 163° C. (dec): partial $^1$H-NMR (D$_2$O; 400 MHz) δ8.09 (s, 4 H), 7.71 (s, 4 H), 7.43 (s, 2 H), 5.03 (d, 2 H), and 5.00 ppm (d, 2 H); $^{13}$C-NMR (DMSO-d$_6$; 100 MHz) δ168.7, 138.1, 137.2, 137.1, 127.8, 125.0, 121.7, 99.9, 99.7, 77.6, 77.4, 77.0, 74.3, 73.4, 72.9, 70.9, 67.6, and 66.3 ppm; mass spectrum (electrospray) (m-zNa)/z 632.8 (m - 7Na)$^{7-}$, 742.1 (m—6Na)$^{6-}$, and 895.2 (m-5Na)$^{5-}$, and 1124.7 (m- 4)$^{4-}$ Anal. Calcd. for C$_{72}$H$_{76}$N$_2$Na$_{28}$O$_{130}$S$_{28}$.28 H$_2$O: C, 16.97; H, 2.61; N, 0.55, S, 17.62. Found: C, 16.77; N, 2.41; N, 0.59; S, 17.42.

EXAMPLE 24

Step 1

Biphenyl-4,4'-disulfonic Acid Bis{[5-(β-D-cellobiosyloxymethyl)-2-methylphenyl]amide}

To 970 mg (1.28 mmol) of 5-(hepta-O-acetyl-β-D-cellobiosyloxymethyl)-2-methylphenylamine in CH$_2$Cl$_2$ (20 mL) containing 1.0 mL (12.4 mmol) of pyridine was added 225 mg (0.641 mmol) of biphenyl-4,4'-disulfonyl chloride. After stirring at room temperature for 90 min, the reaction mixture was quenched with sat. NaHCO$_3$ and extracted into EtOAc. The bright yellow organic phase was washed with pH 7 buffer, dried (MgSO$_4$), and flash chromatographed (EtOAc/Et$_2$O/CH$_2$Cl$_2$, 1:1:1) to give 504 mg (58% yield) of an orange powder. This material (a total of 675 mg (0.378 mmol) from two separate runs) was dissolved in MeOH (10 mL) and THF (10 mL) and was treated with 6 mL of 1N NaOH. After stirring at room temperature for 12 h, the reaction mixture was quenched with 6 mL of 1N HCl, and was concentrated to ca. 6–8 mL. The resulting precipitate was collected and was washed with 15 mL of H$_2$O and then Et$_2$O. Azeotropic drying with toluene gave 335 mg (74% yield) of a pale yellow powder, mp 230° C. (dec): $^1$H-NMR (DMSO, 400 MHz) δ9.69 (s, 2 H), 7.91 (d, 4 H), 7.75 (d, 4 H), 7.16 (d, 2 H), 7.11 (s, 2 H), 7.10 (d, 2 H), 4.71 (d, 2 H), 4.46 (d, 2 H), 4.24–4.28, 3.77 (d, 2 H), 3.70 (d, 2 H), 3.58–3.64 (m, 2 H), 2.97–3.43 (m, 18 H), and 1.91 ppm (s, 6 H); $^{13}$C-NMR (DMSO, 100 MHz) δ142.2, 140.5, 136.1, 134.4, 132.9, 130.5, 127.8, 127.2, 126.0, 103.2, 101.6, 80.5, 76.7, 76.4, 75.1, 74.9, 73.2, 73.1, 70.0, 69.1, 61.0, 60.4, and 17.2 ppm; mass spectrum ((–)-FAB), m/z 1199.3, 750.2, 514.2. Anal. Calcd. for C$_{52}$H$_{68}$N$_2$O$_{26}$S$_2$.H$_2$O: C, 51.23; H, 5.79; N, 2.30. Found: C, 51.04; H, 5.64; N, 2.29.

Step 2

Biphenyl-4,4'-disulfonic Acid Bis{[2-methyl-5-(hepta-O-sulfato-β-D-cellobiosyloxymethyl}phenyl]amide} Tetradecasodium Salt To 214 mg (0.178 mmol) of biphenyl-4,4'-disulfonic acid bis{[5-(β -D-cellobiosyloxymethyl)-2-methylphenyl]

amide} in DMF (10 mL) was added 1.8 g (12.9 mmol) of sulfur trioxide trimethylamine complex. After stirring for 3 days at 70° C., the reaction mixture was cooled to room temperature, quenched with 10 mL of water, and stirred for 20 min. This was concentrated in vacuo and purified by gel filtration (Sephadex G-10) to give 419 mg of pale tan flakes. The compound was dissolved in a minimal amount of water and passed through an ion exchange column (Dowex 50×8 strongly acidic (Na-form)) to give 350 mg of pale tan flakes after azeotropic drying with toluene: $^1$H-NMR (D$_2$O, 400 MHz) δ7.89 (d, 4 H), 7.81 (d, 4 H), 7.39 (d, 2 H), 7.32 (s, 2 H), 7.25 (d, 2 H), 4.94 (d, 2 H), 4.65–4.87 (m, 8 H), 4.57 (dd, 2 H), 4.18–4.51 (m, 16 H), 3.98–4.05 (m, 4 H), and 1.90 ppm (s, 6 H); $^{13}$C-NMR (D$_2$O, 100 MHz) δ143.8, 138.0, 135.4, 134.9, 131.1, 128.1, 128.0, 127.8, 127.3, 99.9, 98.7, 77.6, 77.3, 77.2, 76.9, 74.3, 73.7, 73.3, 72.93, 70.3, 67.6, 66.6., and 16.4 ppm. Anal. Calcd. for C$_{52}$H$_{54}$N$_2$Na$_{14}$O$_{68}$S$_{16}$.18 H$_2$O; C, 21.14; H, 3.05; N, 0.95. Found: C, 21.17; H, 2.71; N, 0.96.

EXAMPLE 25

Step 1

N,N'-Bis[2-methyl-5-(β-D-glucopyranosyloxymethyl) phenyl]succinamide

To a solution of 879 mg (1.88 mmol) of 5-(tetra-O-acetyl-β -D-glucopyranosyloxymethyl)-2-methylphenylamine and 262 μL (1.88 mmol) of triethylamine in THF (10 mL) was added succinyl chloride (104 μL, 0.94 mmol). After stirring at room temperature for 3 h, the reaction mixture was quenched with MeOH (20 mL), diluted with CH$_2$Cl$_2$, washed with H$_2$O, dried (MgSO$_4$), and concentrated. Crystallization from Et$_2$O gave 741 mg (78%) of a green solid which was used directly in the next reaction. To a solution of 360 mg (0.354 mmol) of the crude product in MeOH (7.5 mL) was added 1N NaOH (3.54 mL, 3.54 mmol). After stirring at 50° C. for 90 min, the reaction mixture was quenched at room temperature with 1N HCl (2.85 mL, 2.50 mmol). After stirring for 1 h at room temperature, the solid was collected to provide 229 mg of the title compound: partial $^1$H-NMR (DMSO-d$_6$, 300 MHz) δ941 (s, 2H), 7.36 (s, 2H), 7.17 (d, 2H), 7.12 (d, 2H), 4.78 (d, 2 H), 4.50 (d, 2 H), 4.22 (d, 2 H), 3.69 (d, 2 H), 2.67 (s, 4 H), and 2.18 ppm (s, 6 H).

Step 2

N,N'-Bis[2-methyl-5-(2,3,4,6-tetra-O-suifato-β -D-glucopyranosyloxymethyl)phenyl]succinamide Octasodium Salt A solution of 229 mg (0.337 mmol) of N,N'-bis[2-methyl-5-(β -D-glucopyranosyloxymethyl)phenyl]succinamide and sulfur trioxide trimethylamine complex (2.11 g, 15.2 mmol) in DMF (30 mL) was stirred at 50° C. overnight. The reaction mixture was quenched with H$_2$O (10 mL) and concentrated to an oily solid. The solid was removed and rinsed with a very small amount of H$_2$O. The combined flitrates were concentrated and partially purified by repeated Sephadex G-10 chromatography (H$_2$O elution) and then by dialysis using a 500 MW cut off bag. A small amount of trimethylammonium sulfate was still seen by NMR. Cation exchange was effected with a column of Dowex 50×8 strongly acidic (Na form) resin (H$_2$O eluton) to provide 249 mg (49% yield) of the title compound as an off-white solid, mp >200° C.: partial $^1$H-NMR (D$_2$O, 400 MHz) δ7.39 (d, 2 H), 7.37 (d, 2 H), and 4.55 ppm (t, 2 H); $^{13}$C-NMR (D$_2$O, 100 MHz) δ173.9, 134.82, 134.80, 134.3, 130.8, 127.6, 126.7, 98.8, 75.9, 75.5, 73.4, 72.4, 70.5, 67.8, 31.0, and 16.7 ppm; mass spectrum ((−) FAB) mz 1472.6 (M-Na)$^-$, 1370.7 (m-Na-NaSO$_3$+H)$^-$, 765.9, and 564.8. Anal. Calcd. for C$_{32}$H$_{36}$N$_2$Na$_8$O$_{38}$S$_8$.2 Na$_2$SO$_4$.6 H$_2$O: C, 20.34; H, 2.54; N, 1.48. Found: C, 20.19; H, 2.22; N, 1.39.

EXAMPLE 26

Step 1

N-[5-(Hepta-O-acetyl-β-D-maltosyloxymethyl)-2-methylphenyl]- 3-nitrobenzamide

To a stirred mixture of 5-(hepta-O-acetyl-β-maltosyloxymethyl)-2-methylphenylamine (1.90 g, 2.52 mmol) and pyridine (0.22 g, 2.77 mmol) in CH$_2$Cl$_2$ (10 mL) was added 3-nitrobenzoyl chloride (0.51 g, 2.77 mmol). After 18 h, the mixture was diluted with EtOAc, washed with sat. NaHCO$_3$, H$_2$O, and brine, dried (MgSO$_4$), and concentrated. Purification by flash chromatography (1:1 EtOAc/hexane) gave 2.00 g (88%) of the title compound as a white foam. $^1$H-NMR (DMSO-d$_6$, 400 MHz) δ10.28 (s, 1 H), 8.80 (s, 1 H), 8.45 (dd, 1 H), 8.42 (d, 1 H), 7.84 (m, 1 H), 7.28 (d, 1 H), 7.25 (s, 1 H), 7.10 (d, 1 H), 5.30 (m, 2 H), 5.20 (t, 1 H), 5.05 (t, 1 H), 4.85 (d, 1 H), 4.80 (m, 1 H), 4.75 (m, 2 H), 4.56 (d, 1 H), 4.40 (dd, 1 H), 4.19 (m, 2 H), 4.0 (m, 4 H), 2.20 (s, 3 H), and 2.00 ppm (m, 21 H). Anal. Calcd. for C$_{41}$H$_{48}$N$_2$O$_{21}$: C, 54.42; H, 5.35; N, 3.10. Found: C, 54.30; H, 5.27; N, 3.10.

Step 2

N-[5-(β-D,Maltosyloxymethyl)-2-methylphenyl-3-nitrobenzamide

To a stirred solution of N-[5-(hepta-O-acetyl-β-D-maltosyloxy)-2-methylphenyl] -3-nitrobenzamide (2.00 g, 2.21 mmol) in MeOH (20 mL) was added 25 wt % NaOMe in MeOH (5.10 mL, 22.10 mmol). After 3 h, 10 g of Amberlite IR-120 (H$^+$) ion exchange resin was added. The mixture was filtered and the tiltrate was concentrated to give 1.30 g (96%) of the title compound as a white solid, mp 166°–168° C.: $^1$H-NMR (DMSO-d$_6$, 400 MHz) δ10.37 (s, 1 H), 8.80 (t, 1 H), 8.43 (m, 2 H), 7.85 (m, 1 H), 7.35 (s, 1 H), 7.25 (m, 2 H), 5.00 (d, 1 H), 4.85 (d, 1 H), 4.57 (d, 1 H), 4.30 (d, 1 H), 3.75 (m, 2 H), 3.60 (m, 2 H), 3.40 (m, 6 H), 3.10 (m, 2 H), and 2.21 ppm (s, 3 H); mass spectrum m/e 609 (M-H).

Step 3

N-[5-(Hepta-O-sulfato-β-D-maltosyloxy)-2-methylphenyl]-3-nitrobenzamide Heptasodium Salt A mixture of N-[5-(β-D-maltosyloxymethyl)-2-methylphenyl]-3-nitrobenzamide (1.27 g, 2.08 mmol) and sulfur trioxide trimethylamine complex (10.13 g, 72.79 mmol) in DMF (10 mL) was heated at 70°–75° C. for 4 days. The mixture was cooled, MeOH was added, and the mixture was filtered. The filtrate was concentrated, taken up in MeOH, and passed through a Sephadex LH-20-100 column (1:1 MeOH/CHCl$_3$; 0.1% Et$_3$N). The fractions were concentrated and passed through a Sephadex G-10 gel filtration column (H$_2$O) to give a brown oil. Further purification by reverse phase chromatography (C-18; H$_2$O), flash chromatography (5:0.1: 0.5 CH$_3$CN/H$_2$O/Et$_3$N), and ion exchange on Sephadex SP C-25 (Na$^+$) gave 1.10 g (40%) of the title compound as a white solid, mp 168°–170° C.: $^1$H-NMR (D$_2$, 400 MHz) δ8.82 (t, 1 H), 8.52 (m, 1 H), 8.38 (m, 1 H), 7.86 (m, 1 H), 7.45, (s, 2 H), 5.57 (d, 1 H), 4.99 (d, 1 H), 4.95 (d, 1 H), 4.80 (m, 2 H), 4.62 (t, 1 H), 4.55 (s, 1 H), 4.46 (m, 1 H), 4.30 (m, 4 H), 4.18 (m, 1 H), 4.05 (m, 1 H), and 2.31 ppm (s, 3 H); mass spectrum m/z 1323. Anal. Calcd. for $C_{27}H_{27}N_2Na_7O_{35}S_7 \cdot 3H_2O$: C, 23,52; H, 2.41; N, 2.03. Found: C, 22.70; H, 2.69; N, 1.72.

Step 4

3-[N-[5-(Hepta-O-sulfato-β-D-maltosyloxy)-2-methylphenyl]phenylamine Heptasodium Salt A solution of N-[5-(hepta-O-sulfato-β-D-maltosyloxy)-2-methylphenyl]-3-nitrobenzamide heptasodium salt (0.60 g, 0.45 mmol) in MeOH, $H_2O$, and pyridine was hydrogenated at atmospheric pressure over 10% Pd/C for 6 h. The catalyst was removed by filtration, and the filtrate was concentrated and passed through a Sephadex SP-C25 ($Na^+$) ion exchange column to give 0.40 g (68%) of the title compound as a white solid, mp 232°–234° C. (dec): $^1$H-NMR (D20,300 MHz) δ7.20 (m, 6 H), 6.93 (m, 1 H), 5.42 (d, 1 H), 4.75 (m, 2 H), 4.60 (m, 3 H), 4.48 (m, 2 H), 4.40 (dd, 2 H), 4.30 (t, 1 H), 4.15 (m, 2 H), 4.05 (m, 3 H), 3.95 (m, 2 H), and 2.15 ppm (s, 3 H).

Step 5

3,3'-[N,N'-Ureido]bis[{N-{2-methyl-5-(hepta-O-sulfato-β-D-malosyloxylmethyl)phenyl]}benzamide Tetradecasodium Salt To a stirred mixture of 3-[N-[5-(hepta-O-sulfato-β-D-maltosyloxy)-2-methylphenyl]]phenylamine heptasodium salt (440 mg, 0.34 mmol) and pyridine (5 mL) was added triphosgene (20 mg, 0.057 mmol). Stirring was continued at room temperature for 18 h. The mixture was concentrated, passed through a Sephadex G-10 gel filtration column, and a Sephadex SP-C25 ($Na^+$) ion exchange column. The fractions were concentrated and triturated with MeOH to give 350 mg (79%) of the title compound as an off-white solid, mp 220°° C. (dec): $^1$H-NMR ($D_2O$, 400 MHz) δ 7.61 (d, 2 H), 7.59 (s, 2 H), 7.50 (m, 2 H), 7.43 (m, 8 H), 7.29 (d, 2 H), 5.54 (d, 2 H), 4.95 (t, 4 H), 4.80 (m, 2 H), 4.61 (t, 2 tt), 4.52 (dd, 2 H), 4.44 (t, 4 H), 4.30 (m, 12 H), 4.20 (m, 2 H), 3.98 (t, 2 H), and 2.28 ppm (s, 6 H); $^{13}$C-NMR ($D_2O$, 100 MHz) δ 169.8, 135.3, 135.1, 134.8, 134.4, 131.1, 130.0, 128.1, 126.9, 122.3, 121.7, 117.6, 94.7, 77.6, 76.6, 75.0, 73.7, 73.3, 73.1, 72.5, 69.8, 67.8, 66.0, and 16.8 ppm; mass spectrum m/z 1797. Anal. Calcd. for $C_{55}H_{56}N_4Na_{14}O_{67}S_{14} \cdot 18H_2O$: C, 22.47; H, 3.15; N, 1.91. Found: C, 22.11; H, 2.81; N, 1.59.

EXAMPLE 27

Step 1

N,N'-Bis{3-[2-methyl-5-(hepta-O-acetyl-β-D-maltosyloxymethyl)phenylcarbamoyl]phenyl} isophthalamide To a stirred mixture of 3-amino-[5-(hepta-O-acetyl-β-D-maltosyloxymethyl)-2-methylphenyl]benzamide (1.0 g, 1.143 mmol) and triethylamine (0.12 g, 1.143 mmol) in $CH_2Cl_2$ (5 mL) was added isophthaloyl dichloride (0.12 g, 0.572 mmol). After 18 h, water was added and the layers were separated. The organic phase was washed with saturated aqueous $NaHCO_3$ and brine, dried ($MgSO_4$), and concentrated. Purification by flash chromatography gave 0.57 g (53%) of product as a white solid, mp 178°–180 ° C.: $^1$H-NMR (DMSO-$d_6$, 300 MHz) δ10.60 (s, 2 H), 9.90 (s, 2 H), 8.60 (s, 1 H), 8.37 (s, 2 H), 8.21 (dd, J=1.5, 7.7 Hz, 2 H), 8.05 (d, J=7.7 Hz, 2 H), 7.75 (m, 3 H), 7.52 (t, J=7.9 Hz, 2 H), 7.25 (m, 4 H), 7.10 (d, J=7.8 Hz, 2 H), 5.30 (m, 5 H), 5.03 (m, 3 H), 4.80 (m, 4 H), 4.70 (m, 4 H), 4.50 (d, J=12.5 Hz, 2 H), 4.40 (d, J=12.5 Hz, 2 H), 4.20 (m, 4 H), 3.95 (m, 8 H), 2.20 (s, 6 H), and 1.90–2.00 ppm (m, 42 H).

Step 2

N,N'-Bis{3-[2-methyl-5-(β-D-maltosyloxymethyl)phenylcarbamoyl]phenyl} isophthalamide To a warmed solution of N,N'-bis{3-[2-methyl-5-(hepta-O-acetyl-β-D-maltosyloxymethyl)phenylcarbamoyl]phenyl}isophthalamide (0.572 g, 0.304 mmol) in MeOH (10 mL) was added 25 wt % NaOMe in MeOH (0.5 mL, 2.13 mmol). After 2 h, Amberlite IR-120 ($H^+$) resin was added. The mixture was filtered and concentrated to give 0.300 g (77%) of product as a white solid, mp 232°–234° C.: $^1$H-NMR (DMSO-$d_6$, 300 MHz) δ10.65 (s, 2 H), 9.90 (s, 2 H) 8.60 (s, 1 H), 8.35 (s, 2 H), 8.21 (dd, J=1.5, 7.7 Hz, 2 H), 8.05 (d, J=7.7 Hz, 2 H), 7.70 (m, 2 H), 7.50 (t, J= 7.9 Hz, 2 Iq), 7.35 (s, 2 H), 7.20 (m, 5 H), 5.01 (d, J=3.9 Hz, 2 H), 4.80 (d, J=12.5 Hz, 2 H), 4.50 (d, J=12.5 Hz, 2 H), 4.30 (d, J=7.9 Hz, 2 H), 3.20–3.75 (m, 26 H), 3.10 (m, 4 H), 2.20 (s, 6 H).

Step 3

N,N'-Bis{3-[2-methyl-5-(hepta-O-sulfalo-β-D-maltosyloxymethyl)phenylcarbamoyl)phenyl] isophthalamide Tetradecasodium Salt A mixture of N,N'-bis{3-[2-methyl-5-(β -D-maltosyloxymethyl)phenylcarbamoyl]phenyl}isophthalamide (0.30 g, 0.232 mmol) and sulfur trioxide pyridine complex (2.60 g, 16.267 mmol) in DMF (10 mL) was stirred at room temperature for 2 days. The mixture was concentrated, purified on a Sephadex LH-20-100 column (0.5% $Et_3N$/ DMF), and converted to a sodium salt with Sephadex SP-C25 ion exchange resin to give 0.200 g (31%) of product as an off white solid, mp 222° C. (dec): $^1$H-NMR ($D_2O$, 400 MHz) δ8.45 (s, 1 H), 8.35 (brs, 2 H), 8.10 (brs, 2 H), 7.95 (d, J=7.9 Hz, 2 H), 7.85 (d, 7.9 Hz, 2 H), 7.75 (brs, 2 H), 7.57 (brs, 2 H), 7.35 (brs, 5 H), 4.75 (m, 4 H), 4.45 (m, 4 H), 4.30 (m, 4 H), 4.10 (m, 4 H), 3.80 (m, 4 H), 3,57 (m, 4 H), 3.28 (m, 8 H), and 2.20 ppm (s, 6 H); $^{13}$C-NMR ($D_2O$, 100 MHz) δ160, 137, 134, 130, 128, 120, 102, 96, 75, 74, 72, 62, 56, 49, 18 ppm.

We claim:

1. A compound of formula I

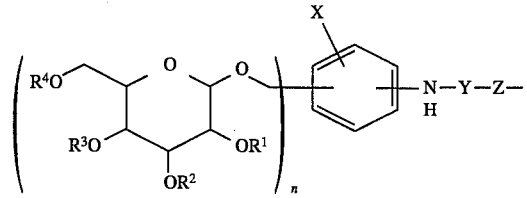

33

-continued

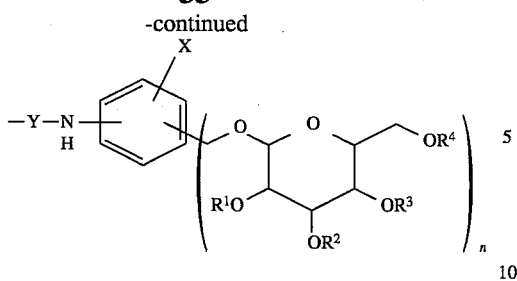

wherein each of $R^1$, $R^2$, $R^3$, and $R^4$ are, independently, H, $SO_3M$, or a sugar group having the structure:

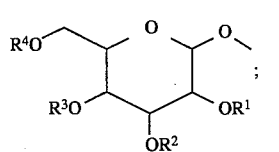

and each oligosaccharide group of the structure

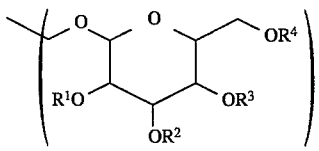

contains from 1 to 3 sugar groups;

M is lithium, sodium, potassium, or ammonium;

n is 1 or 2;

X is a hydrogen, halogen, lower alkyl having 1 to 6 carbon atoms, or lower alkoxy having 1 to 6 carbon atoms;

Y is carbonyl or sulfonyl;

Z is alkyl having from 1 to 12 carbon atoms,

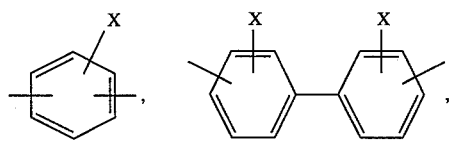

34

-continued

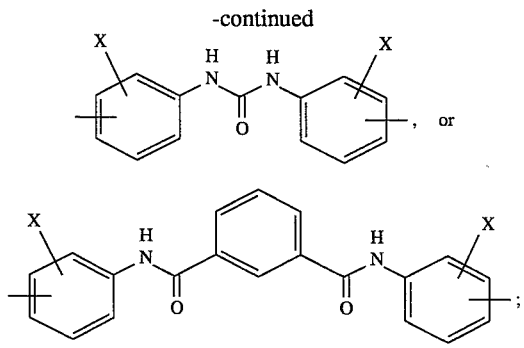

and X is as defined above;

or a pharmaceutically acceptable salt thereof.

2. A compound according to claim 1 of formula I

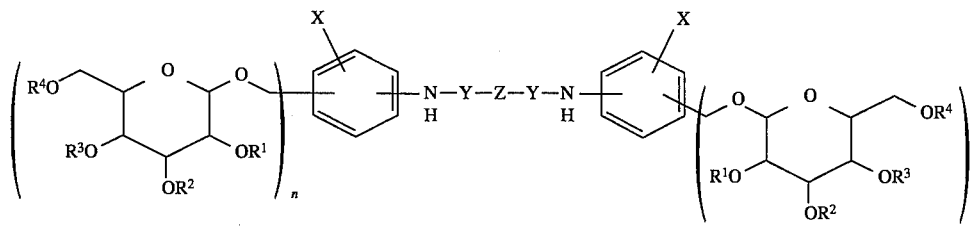

wherein each of $R^1$, $R^2$, $R^3$, and $R^4$ are, independently, H, $SO_3M$, or

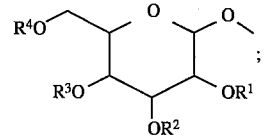

and each oligosaccharide group of the structure

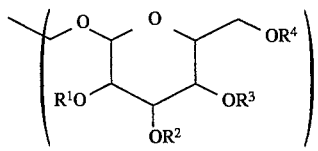

contains 1 or 2 sugar groups;

M is lithium, sodium, potassium, or ammonium;

n is 1 or 2;

X is a hydrogen, halogen, lower alkyl having 1 to 6 carbon atoms, or lower alkoxy having to 6 carbon atoms;

Y is carbonyl or sulfonyl;

Z is alkyl having from 1 to 12 carbon atoms,

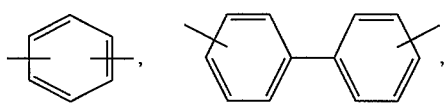

-continued

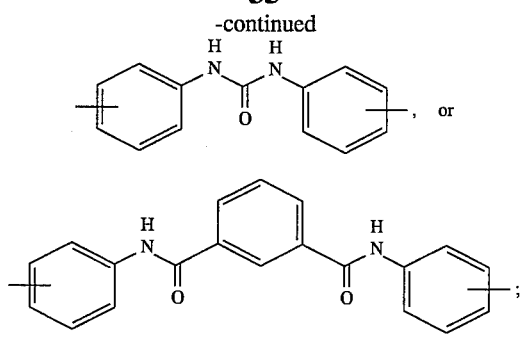

or a pharmaceutically acceptable salt thereof.

3. A compound according to claim 2 which is dodecanedioic acid bis{[2-methyl-5-(hepta-O-sulfato-β-D-cellobiosyloxymethyl)phenyl]amide}tetradecasodium salt or a pharmaceutically acceptable salt thereof.

4. A compound according to claim 2 which is 2 N,N'-bis[5-(hepta-O-sulfato-β-D-cellobiosyloxymethyl)-2-methylphenyl]-terephthalamide tetradecasodium salt or a pharmaceutically acceptable salt thereof.

5. A compound according to claim 2 which is biphenyl-4,4'-dicarboxylic acid bis{[5-(hepta-O-sulfato-β-D-cellobiosyloxymethyl)-2-methylphenyl]amide} tetradecasodium salt or a pharmaceutically acceptable salt thereof.

6. A compound according to claim 2 which is N,N'-bis[5-(hepta-O-sulfato-β-D-cellobiosyloxymethyl)-2-methylphenyl]isophthalamide tetradecasodium salt; or a pharmaceutically acceptable salt thereof.

7. A compound according to claim 2 which is decanedioic acid bis{[ 3,5-bis(hepta-0-sulfato-β-D-cellobiosyloxymethyl)phenyl]amide octacosasodium salt or a pharmaceutically acceptable salt thereof.

8. A compound according to claim 2 which is biphenyl-4,4'-dicarboxylic acid bis{[3,5-bis(hepta-O-sulfato-β-D-cellobiosyloxymethyl)phenyl]amide}octacosa-sodium salt or a pharmaceutically acceptable salt thereof.

9. A compound according to claim 2 which is biphenyl-4,4'-dicarboxylic acid bis{[3,5-bis-(hepta-O-sulfato-β-D-lactosyloxymethyl)phenyl]amide} octacosasodium salt or a pharmaceutically acceptable salt thereof.

10. A compound according to claim 2 which is biphenyl-4,4'-dicarboxylic acid bis{[3,5-(bis-(hepta-O-sulfato-β-D-maltosyloxymethyl)phenyl]amide} octacosasodium salt or a pharmaceutically acceptable salt thereof.

11. A compound according to claim 2 which is biphenyl-4,4'-dicarboxylic acid bis{[3,5-bis-(tetra-O-sulfato-β-D-glucosyloxymethyl)phenyl]amide} hexadecasodium salt or a pharmaceutically acceptable salt thereof.

12. A compound according to claim 2 which is biphenyl-4,4'-dicarboxylic acid bis{[2-chloro-5-(hepta-O-sulfato-β-D-cellobiosyloxymethyl)phenyl]amide} tetradecasodium salt or a pharmaceutically acceptable salt thereof.

13. A compound according to claim 2 which is biphenyl-4,4'-dicarboxylic acid bis{[4-chloro- 2-(hepta-O-sulfato-β-D-cellobiosyloxymethyl)phenyl]amide} tetradecasodium salt or a pharmaceutically acceptable salt thereof.

14. A compound according to claim 2 which is N,N'-bis [3,5 -bis(hepta-O-sulfato-β-D-cellobiosyloxymethyl)phenyl]succinamide octacosasodium salt or a pharmaceutically acceptable salt thereof.

15. A compound according to claim 2 which is N,N'-bis [3,5 -bis(hepta-O-sulfato-β-D-cellobiosyloxymethyl)phenyl]terephthalamide octacosasodium salt or a pharmaceutically acceptable salt thereof.

16. A compound according to claim 2 which is biphenyl-4,4'-disulfonic acid bis{[2-methyl-5-(hepta-O-sulfato-β-D-cellobiosyloxymethyl)phenyl]amide} tetradecasodium salt or a pharmaceutically acceptable salt thereof.

17. A compound according to claim 2 which is N,N'-bis [2-methyl-5( 2,3,4,6-tetra-O-sulfato-β-D-glucopyranosyloxymethyl)phenyl]succinamide octasodium salt or a pharmaceutically acceptable salt thereof.

18. A compound according to claim 2 which is 3,3'-[1,3-ureido]-bis{N-[ 2-methyl-5-(hepta-O-sulfato-β-D-maltosyloxymethyl)phenyl]}benzamide tetradecasodium salt or a pharmaceutically acceptable salt thereof.

19. A compound according to claim 2 which is 3,3'-(N, N'-ureido)bis-({ N-2-chloro-5-(hepta-O-sulfato-β-D-cellobiosyloxymethyl)phenyl}benzamide) tetradecasodium salt or a pharmaceutically acceptable salt thereof.

20. A compound according to claim.2 which is N,N'-bis{3-[2-methyl- 5-(hepta-O-sulfato-β-D-maltosyloxymethyl)phenylcarbamoyl]phenyl}isophthalamide tetradecasodium salt or a pharmaceutically acceptable salt thereof.

21. A method of treating a human suffering from a condition which is characterized by excessive smooth muscle proliferation, the method comprising administering to the human an effective amount of the compound formula I

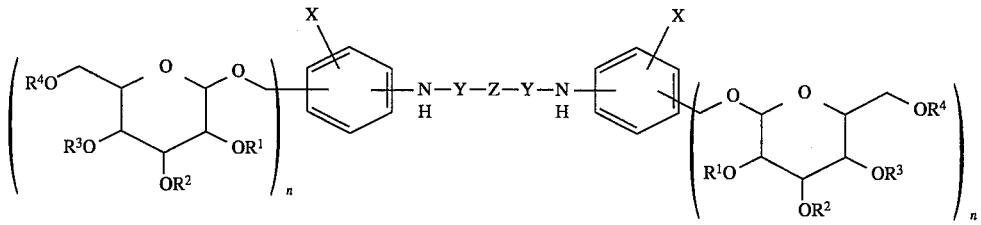

wherein each of $R^1$, $R^2$, $R^3$, and $R^4$ are, independently, H, $SO_3M$, or a sugar group having the structure:

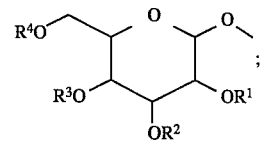

and each oligosaccharide group of the structure

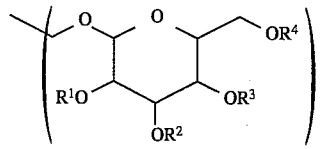

contains from 1 to 3 sugar groups;

M is lithium, sodium, potassium, or ammonium;

n is 1 or 2;

X is a hydrogen, halogen, lower alkyl having 1 to 6 carbon atoms, or lower alkoxy having 1 to 6 carbon atoms;

Y is carbonyl or sulfonyl;

Z is alkyl having from 1 to 12 carbon atoms,

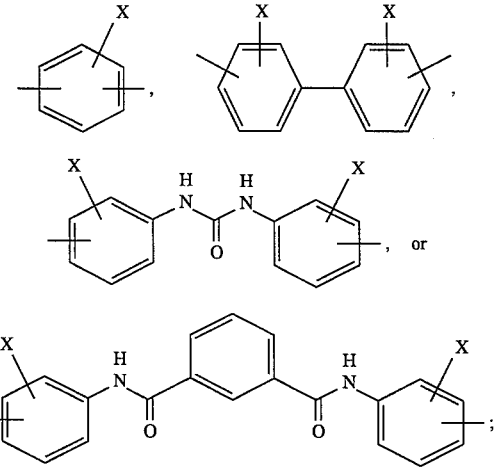

and X is as defined above;
or a pharmaceutically acceptable salt thereof.

22. The method of claim 21 wherein the disease or condition which is characterized by excessive smooth muscle proliferation is restenosis.

23. A pharmaceutical composition comprising an effective amount of a compound of formula I

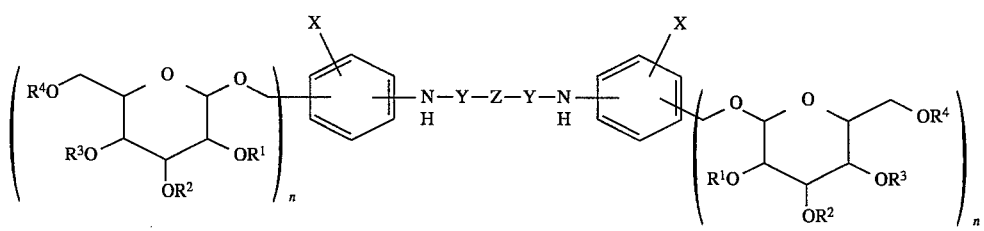

wherein each of $R^1$, $R^2$, $R^3$, and $R^4$ are, independently, H, $SO_3M$, or a sugar group having the structure:

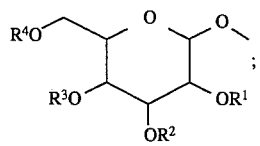

and each oligosaccharide group of the structure

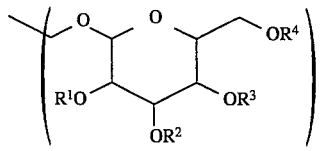

contains from 1 to 3 sugar groups;

M is lithium, sodium, potassium, or ammonium;

n is 1 or 2;

X is a hydrogen, halogen, lower alkyl having 1 to 6 carbon atoms, or lower alkoxy having 1 to 6 carbon atoms;

Y is carbonyl or sulfonyl;

Z is alkyl having from 1 to 12 carbon atoms,

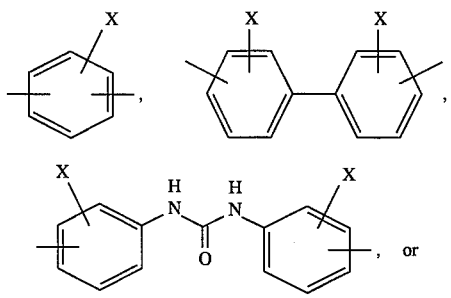

-continued

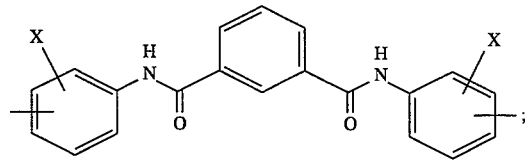

and X is as defined above;
or a pharmaceutically acceptable salt thereof.

* * * * *